United States Patent [19]
Liu et al.

[11] Patent Number: 6,127,556
[45] Date of Patent: Oct. 3, 2000

[54] EPOXIDE FORMATION BY CONTINUOUS IN-SITU SYNTHESIS PROCESS

[75] Inventors: Chin Liu, Vernon Hills; John S. Ng, Chicago; James R. Behling, Lindenhurst; Arthur L. Campbell, Glenview, all of Ill.

[73] Assignee: G. D. Searle & Co., Chicago, Ill.

[21] Appl. No.: 08/991,598

[22] Filed: Dec. 16, 1997

Related U.S. Application Data

[60] Provisional application No. 60/033,801, Dec. 31, 1996.

[51] Int. Cl.[7] .................................................. C07D 301/02
[52] U.S. Cl. .......................... 549/519; 549/552; 549/553
[58] Field of Search .................................... 549/519, 552, 549/553

[56] References Cited

U.S. PATENT DOCUMENTS

| | | | |
|---|---|---|---|
| 4,268,688 | 5/1981 | Tinker et al. | 560/177 |
| 4,990,669 | 2/1991 | Reetz et al. | 564/391 |
| 5,550,291 | 8/1996 | Beaulieu et al. | 564/357 |

FOREIGN PATENT DOCUMENTS

| | | |
|---|---|---|
| 93/23388 | 11/1993 | WIPO . |
| 95/14653 | 6/1995 | WIPO . |
| 96/17821 | 6/1996 | WIPO . |

OTHER PUBLICATIONS

Ng et al, Tetrahedron, vol. 51 (23), pp. 6397–6410, 1995.
Barluenger et al, J. Org. Chem., vol. 60 (21), pp. 6696–6699, 1995.
Roberts, et al., "Rational Design of Peptide–Based HIV Proteinase Inhibitors," Science, vol. 248, 358–361, (1990).
Krohn, et al., "Novel Binding Mode of Highly Potent HIV–Proteinase Inhibitors Incorporating the R–Hydroxyethylamine Isotere," J. Med. Chem., vol. 34, 3340–3342, (1991).
Getman, et al., "Discovery of a Novel Class of Potent HIV–1 Protease Inhibitors Containing the (R)–(Hydroxyethyl) urea Isostere," J. Med. Chem., vol. 36, 288–291, (1993).
Reetz, et al., "Protective Group Tuning in the Steroselective Conversion of α–Amino Aldehydes into Aminoalkyl Epoxides," Tett. Lett., vol. 30, No. 40, 5425–5428, (1989).
Matteson, et al., "Synlett., (Bromomethyl)lithium: Efficient In Situ Reactions," John Wiley & Sons, Inc. (1991).
Green, et al., "Protective Groups In Organic Synthesis," 2nd Ed., John Wiley & Sons, Inc. (1991).
Reetz, et al., "Stereoselective Synthesis of β–Amino Acids," Angew Chem. Int. Ed. Engl., vol. 26, No. 11, 1141–1143, (1987).
Parikh, et al., "Sulfur Trioxide in the Oxidation of Alcohol by Dimethyl Sulfoxide," J. Am. Chem. Soc., 89, 5505–5507 (1967).
Liu, et la., "Development of a Large–Scale Process for an HIV Protease Inhibitor," Organic Process Research & Development, vol. 1, 45–54, 1997.
Abstract, Liu et al., "Development of a Large–Scale Process for HIV Protease Inhibitors," Database Advances ACS Abstracts, American Chemical Society, Dec. 15, 1996.
Beaulieu et al., "Large Scale Preparation of (2S, 3S)–N–Boc–3–Amino–1,2–Epoxy–4–Phenylbutane: A Key Building Block for HIV–Protease Inhibitors," Tetrahedron Letters, vol. 36, No. 19, pp. 3317–3320 (1995).
Beaulieu et al., "Preparation of Aminoalkyl Chlorhydrin Hydrochlorides: Key Building Blocks for Hydroxyethylamine–Based HIV Protease Inhibitors," *J. Org. Chem.* 61, 3625–3645 (1996).

*Primary Examiner*—Ba K. Trinh
*Attorney, Agent, or Firm*—Banner & Witcoff, Ltd.

[57] ABSTRACT

In a method of preparing an aminoepoxide wherein a protected aminoaldehyde is reacted with a halomethyl organometallic reagent in an appropriate solvent at a temperature above −80° C., wherein said halomethyl organometallic reagent is formed by reaction between an organometallic reagent and a dihalomethane, the improvement comprising flowing said protected aminoaldehyde into a mixing zone maintained at a temperature below 0° C., also flowing said halomethyl organometallic reagent in said mixing zone for contacting in said mixing zone with said protected aminoaldehyde and also withdrawing from said mixing zone reaction products of said protected aminoaldehyde and said halomethyl organometallic reagent.

17 Claims, No Drawings

EPOXIDE FORMATION BY CONTINUOUS IN-SITU SYNTHESIS PROCESS

This application claims priority benefits under 35 U.S.C. 119 of provisional application No. 60/033,801 filed Dec. 31, 1996.

BACKGROUND OF THE INVENTION

Synthesis of many pharmaceuticals which contain a hydroxyethylamine isostere, such as the aspartyl protease HIV protease inhibitors, involves an amine opening of an epoxide intermediate. Such pharmaceuticals contain chiral centers that can be introduced in the synthesis of the drug by utilizing a chiral epoxide intermediate. The preparation of such epoxides, including chiral epoxides, may require a multi-step synthesis starting from a L-amino acid such as L-phenylalanine or an amino acid derivative such as an alcohol like phenylalaninol. Historically, such epoxides were prepared by methods that involved reduction of a chloromethylketone intermediate. This can lead to low overall yields. The chloromethylketone was frequently prepared by a process that required the use of the highly toxic and highly explosive diazomethane. Because of the nature of diazomethane, its use generally is not applicable to the large scale (multikilogram) production of either intermediates or final products. Furthermore the overall yield for diastereoselective reduction of chloroketones, especially those used in the preparation of HIV-protease inhibitors, can be low.

An improved process for the preparation of such epoxide intermediates is disclosed in WO 93/23388 and WO 95/14653. The process involves the cold temperature reaction of a halomethyl lithium reagent with an aldehyde intermediate. This process is particularly suited for the preparation of chiral epoxide intermediates but it requires the cooling of large reactors containing large quantities of solvent and reagents. A less convenient and less efficient method of generating a halomethyl lithium reagent from lithium metal for reaction with an alpha-aminoaldehyde compound is disclosed in WO 9617821. The present invention relates to an improvement in this halomethyl organometallic reagent addition to an aldehyde carbonyl method of preparing epoxides. In particular, the invention is directed to the diastereoselective production of chiral epoxides utilizing a continuous flow process wherein a reagent or reagents can be added with or without priming more or less at the same time (more or less simultaneously) in an uninterrupted fashion.

Roberts et al, Science, 248, 358 (1990), Krohn et al, J. Med. Chem. 344, 3340 (1991) and Getman, et al, J. Med. Chem., 346, 288 (1993) have previously reported synthesis of HIV-protease inhibitors containing the hydroxyethylamine, hydroxyethylurea or hydroxyethylsulfonamide isostere which included the opening of an epoxide generated in a multi-step synthesis starting from an amino acid. These methods also contain steps which include diazomethane as a reagent in the synthesis of chloromethylketones and the reduction of amino chloromethyl ketone intermediates to an amino halo-alcohol prior to formation of the epoxide. The overall yields of these syntheses are low. In addition, as noted above the use of toxic and explosive diazomethane prevents such methods from being useful for the commercial or pilot plant production of drugs. Thus, in spite of the prior art's ability to synthesize HIV-protease inhibitors, more efficient, environmentally acceptable and commercially desirable processes are needed.

Tinker et al U.S. Pat. No. 4,268,688 disclose a catalytic asymmetric hydroformylation process for preparing optically active aldehydes from unsaturated olefins. Similarly, Reetz et al U.S. Pat. No. 4,990,669 disclose the formation of optically active alpha amino aldehydes through the reduction of alpha amino carboxylic acids or their esters with lithium aluminum hydride followed by oxidation of the resulting protected beta amino alcohol by dimethyl sulfoxide/oxalyl chloride or chromium trioxide/pyridine. Alternatively, protected alpha amino carboxylic acids or esters thereof can be reduced with diisobutylaluminum hydride to form the protected amino aldehydes.

Reetz et al (Tet. Lett., 30, 5425 (1989)) disclose the use of sulfonium and arsonium ylides and their reactions with protected alpha-amino aldehydes to form aminoalkyl epoxides. This method suffers from the use of highly toxic arsonium compounds or the use of combination of sodium hydride and dimethyl sulfoxide which is extremely hazardous on a large scale. Matteson, et. al., Syn. Lett., 1991, 631 reported the addition of chloromethyllithium or bromomethyllithium to achiral or racemic aldehydes.

SUMMARY OF THE INVENTION

The present invention relates to a process for the preparation of epoxides, in particular chiral epoxides, from aldehydes using a halomethyl lithium reagent which is continuously synthesized in situ at cold temperatures. The continuous in situ synthesis process is more versatile, controllable, efficient and cost effective than the corresponding batch or stepwise synthesis process used in the prior art.

In particular, in accordance with a preferred embodiment of the present invention, an aldehyde of the invention, as described in more detail below, is flowed into and through a mixing zone within which the aldehyde is maintained at a temperature of between about −80° C. to 0° C., preferably between about −60° C. to −10° C. and more preferably between −40° C. to −15° C.; while the aldehyde is flowing through the mixing zone, a dihalomethane reagent and an organometallic (lithium) reagent are added in a manner which generates continuously in situ a halomethyl lithium reagent, and a chiral epoxide is subsequently recovered from the output of the mixing zone.

DETAILED DESCRIPTION OF THE INVENTION

This invention relates to a method of preparing HIV protease inhibitors that allows the preparation of commercial quantities of intermediates of the formula

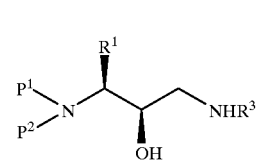

(I)

wherein $R^1$ is selected from alkyl, aryl, cycloalkyl, cycloalkylalkyl, arylalkyl and arylthioalkyl, which are optionally substituted with a group selected from alkyl, halogen, $NO_2$, $OR^9$ or $SR^9$, where $R^9$ represents hydrogen or alkyl; and $R^3$ represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical. Preferably, $R^3$ represents radicals as defined above which contain no alpha-branching, e.g., as in an isopropyl radical or a t-butyl radical. The preferred radicals are those which contain a —$CH_2$— moiety between the nitrogen and the remaining portion of the radical. Such preferred groups include, but are not limited to, benzyl, isobutyl, n-butyl, isoamyl, cyclohexylmethyl and the like.

$P^1$ and $P^2$ independently are selected from amine protecting groups, including but not limited to, arylalkyl, substituted arylalkyl, cycloalkenylalkyl and substituted cycloalkenylalkyl, allyl, substituted allyl, acyl, alkoxycarbonyl, aralkoxycarbonyl and silyl. Examples of arylalkyl include, but are not limited to benzyl, orthomethylbenzyl, 2,6-dichlorobenzyl, trityl and benzhydryl, which can be optionally substituted with halogen, alkyl of $C_1$-$C_8$, alkoxy, hydroxy, nitro, alkylene, amino, alkylamino, acylamino and acyl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkylenylalkyl radicals containing cycloalkyls of $C_6$-$C_{10}$. Suitable acyl groups include carbobenzoxy, t-butoxycarbonyl, iso-butoxycarbonyl, benzoyl, substituted benzoyl such as 2-methylbenzoyl, 2,6-dimethylbenzoyl 2,4,6-trimethylbenzoyl and 2,4,6-triisopropylbenzoyl, 1-naphthoyl, 2-naphthoyl butyryl, acetyl, tri-fluoroacetyl, tri-chloroacetyl, phthaloyl and the like.

Additionally, the $P^1$ and/or $P^2$ protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl. The term silyl refers to a silicon atom optionally substituted by one or more alkyl, aryl and aralkyl groups.

Suitable carbamate protecting groups include, but are not limited to, methyl and ethyl carbamate; 9-fluorenylmethyl carbamate; 9-(2-Sulfo)fluorenylmethyl carbamate; 9-(2,7-dibromo)fluorenylmethyl carbamate; 2,7-di-t-butyl-[9-(10, 10-dioxo-10,10,10-tetrahydrothioxanthyl)methyl carbamate; 4-methoxyphenacyl carbamate; 2,2,2-trichloroethyl carbamate; 2-trimethylsilylethyl carbamate; 2-phenylethyl carbamate; 1-(1-adamantyl)-1-methylethyl carbamate; 1,f-dimethyl-2-haloethyl carbamate; 1,1-dimethyl-2,2-dibromoethyl carbamate; 1,1-dimethyl-2,2,2-trichloroethyl carbamate; 1-methyl-1-(4-biphenylyl)-ethyl carbamate; 1-(3,5-di-t-butylphenyl)-1-methylethyl carbamate; 2-(2'- and 4'-pyridyl)ethyl carbamate; 2-(N,N-dicyclohexylcarboxamido)ethyl carbamate; t-butyl carbamate; 1-adamantyl carbamate; vinyl carbamate; allyl carbamate; 1-isopropylallyl carbamate; cinnamyl carbamate; 4-nitrocinnamyl carbamate; 8-quinolyl carbamate; N-hydroxypiperidinyl carbamate; alkyldithio carbamate; benzyl carbamate; p-methoxybenzyl carbamate; p-nitrobenzyl carbamate; p-bromobenzyl carbamate; p-chlorobenzyl carbamate; 2,4-dichlorobenzyl carbamate; 4-methylsulfinylbenzyl carbamate; 9-anthrylmethyl carbamate; diphenylmethyl carbamate; 2-methylthioethyl carbamate; 2-methylsulfonylethyl carbamate; 2-(p-toluenesulfonyl) ethyl carbamate; [2-(1,3-dithianyl)methyl carbamate; 4-methylthiophenyl-2,4-dimethylthiophenyl, 2-phosphonioethyl carbamate; 2-triphenylphosphonioisopropyl carbamate; 1,1-dimethyl-2-cyanoethyl carbamate; m-chloro-p-acyloxybenzyl carbamate; p-(dihydroxyboryl)benzyl carbamate; 5-benziosoxazolylmethyl carbamate; 2-(trifluoromethyl)-6-chromonylmethyl carbamate; m-nitrophenyl carbamate; 3,5-dimethoxybenzyl carbamate; o-nitrobenzyl carbamate; 3,4-dimethoxy-6-nitrobenzyl carbamate; phenyl(o-nitrophenyl) methyl carbamate; phenothiazinyl-(10)-carbonyl derivative; N'-p-toluenesulfonylaminocarbonyl derivative; N'-phenylaminothiocarbonyl derivative t-amyl carbamate; S-benzyl thiocarbamate; p-cyanobenzyl carbamate; cyclobutyl carbamate; cyclohexyl carbamate; cyclopentyl carbamate; cyclopropylmethyl carbamate; p-decyloxybenzyl carbamate; diisopropylmethyl carbamate; 2,2-dimethoxycarbonylvinyl carbamate; o-(N,N-dimethylcarboxamido)benzyl carbamate; 1,1-dimethyl-3-(N,N-dimethylcarboxamido)propyl carbamate; 1,1-dimethylpropynyl carbamate; di(2-pyridyl)methyl carbamate; 2-furanylmethyl carbamate; 2-iodoethyl carbamate; isobornyl carbamate; isobutyl carbamate; isonicotinyl carbamate; p-(p'-methoxyphenylazo)benzyl carbamate; 1-methylcyclobutyl carbamate; 1-methylcyclohexyl carbamate; 1-methyl-1-cyclopropylmethyl carbamate; 1-methyl-1-(3,5-dimethoxyphenyl)ethyl carbamate; 1-methyl-1-(p-phenylazophenyl)ethyl carbamate; and 1-methyl-1-phenylethyl carbamate. T. Greene and P. Wuts ("Protective Groups In Organic Synthesis," 2nd Ed., John Wiley & Sons, Inc. (1991)) describe the preparation and cleavage of such carbamate protecting groups.

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a metal hydroxide or ammonium flouride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chlorie, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Preferably $P^1$ is selected from aralkyl, substituted aralkyl, alkylcarbonyl, aralkylcarbonyl, arylcarbonyl, alkoxycarbonyl and aralkoxycarbonyl, $P^2$ is selected from aralkyl and substituted aralkyl and $R^1$ is selected from aralkyl and substituted aralkyl. Alternatively, when $P^1$ is alkoxycarbonyl or aralkoxycarbonyl, $P^2$ can be hydrogen. More preferably, $P^1$ is t-butoxycarbonyl, phenylmethoxycarbonyl or benzyl, $P^2$ is hydrogen or benzyl and $R^1$ is benzyl.

Protected chiral amino epoxides of the formula

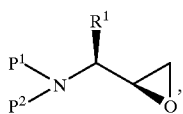

(IV)

protected chiral amino alpha-hydroxycyanides, nitromethylene and acids of the formula

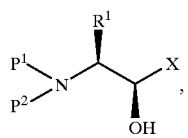

wherein X is —CN, —CH$_2$NO$_2$ or —COOH, protected chiral alpha-aminoaldehyde intermediates of the formula

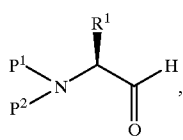

(III)

and protected chiral alpha-amino alcohols of the formula

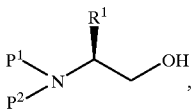

(II)

wherein $P^1$, $P^2$ and $R^1$ are as defined above, are also described herein.

As utilized herein, the term "amino epoxide" alone or in combination, means an amino-substituted alkyl epoxide wherein the amino group can be a primary {substituted with one additional group}, or secondary {substituted with two additional groups} amino group containing substituents selected from hydrogen, and alkyl, aryl, aralkyl, alkenyl, alkoxycarbonyl, aralkoxycarbonyl, cycloalkenyl, silyl, cycloalkylalkenyl radicals and the like and the epoxide can be alpha to the amine. The term "amino aldehyde" alone or in combination, means an amino-substituted alkyl aldehyde wherein the amino group can be a primary, or secondary amino group containing substituents selected from hydrogen, and alkyl, aryl, aralkyl, alkenyl, aralkoxycarbonyl, alkoxycarbonyl, cycloalkenyl, silyl, cycloalkylalkenyl radicals and the like and the aldehyde can be alpha to the amine. The term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, allyl, 1,4-butadienyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkenyl", alone or in combination, means an alkyl radical which contains from about 3 to about 8 carbon atoms and is cyclic and which contains at least one double bond in the ring which is non-aromatic in character. The term "alkynyl", alone or in combination, means a straight-chain hydrocarbon radical having one or more triple bonds and containing from 2 to about 10 carbon atoms. Examples of alkynyl radicals include ethynyl, propynyl, (propargyl), butynyl and the like. The term "cycloalkenylalkyl" means cycloalkenyl radical as defined above which is attached to an alkyl radical, the cyclic portion containing from 3 to about 8, preferably from 3 to about 6, carbon atoms. Examples of such cycloalkenyl radicals include cyclopropenyl, cyclobutenyl, cyclopentenyl, cyclohexenyl, dihydrophenyl and the like. The term "cycloalkyl", alone or in combination, means an alkyl radical which contains from about 3 to about 8 carbon atoms and is cyclic. The term "cycloalkylalkyl" means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like. The term "aryl", alone or in combination, means a carbocyclic aromatic system containing one, two or three rings wherein such rings may be attached together in a pendent manner or may be fused. Examples of "aryl" include phenyl or naphthyl radical either of which optionally carries one or more substituents selected from alkyl, alkoxy, halogen, hydroxy, amino, nitro and the like, as well as p-tolyl, 4-methoxyphenyl, 4-(tert-butoxy) phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. Examples of substituted aralkyl include 3,5-dimethoxybenzyl bromide, 3,4-dimethoxybenzyl bromide, 2,4-dimethoxybenzyl bromide, 3,4,5-trimethoxybenzyl bromide, 4-nitrobenzyl iodide, 2,6-dichlorobenzyl bromide, 1,4-bis(chloromethyl)benzene, 1,2-bis(bromomethyl) benzene, 1,3-bis(chloromethyl)-benzene, 4-chlorobenzyl chloride, 3-chlorobenzyl chloride, 1,2-bis(chloromethyl) benzene, 6-chloropiperonyl chloride, 2-chlorobenzyl chloride, 4-chloro-2-nitrobenzyl chloride, 2-chloro-6-fluorobenzyl chloride, 1,2-bis(chloromethyl)-4,5-dimethylbenzene, 3,6-bis(chloromethyl)durene, 9,10-bis (chloromethyl)anthracene, 2,5-bis(chloromethyl)-p-xylene, 2,5-bis(chloromethyl)-1,4-dimethoxybenzene, 2,4-bis (chloromethyl)anisole, 4,6-(dichloromethyl)-m-xylene, 2,4-bis(chloromethyl)mesitylene, 4-(bromomethyl)- 3,5-dichlorobenzophenone, n-(alpha-chloro-o-tolyl)-benzylamine hydrochloride, 3-(chloromethyl)benzoyl chloride, 2-chloro-4-chloromethyltoluene, 3,4-dichlorobenzyl bromide, 6-chloro-8-chloromethylbenzo-1, 3-dioxan, 4-(2,6-dichlorobenzylsulphonyl)benzylbromide, 5-(4-chloromethylphenyl)-3-(4-chlorophenyl)-1,2,4-oxadiazole, 5-(3-chloromethylphenyl)-3-(4-chlorophenyl)-1,2,4-oxadiazole, 4-(chloromethyl)benzoyl chloride, di(chloromethyl)toluene, 4-chloro-3-nitrobenzyl chloride, 1-(dimethylchlorosilyl)-2-(p,m-chloromethylphenyl)ethane, 1-(dimethylchlorosilyl)-2-(p,m-chloromethylphenyl)ethane, 3-chloro-4-methoxybenzyl chloride, 2,6-bis(chloromethyl)-4-methylphenol, 2,6-bis(chloromethyl)-p-tolyl acetate, 4-bromobenzyl bromide, p-bromobenzoyl bromide, alpha alpha'-dibromo-m-xylene, 3-bromobenzyl bromide, 2-bromobenzyl bromide, 1,8-bis(bromomethyl)naphthalene, o-xylylene dibromide, p-xylylene dibromide, 2,2'-bis (bromomethyl)-1,1'-biphenyl, alpha,alpha'-dibromo-2,5-dimethoxy-p-xylene, benzyl chloride, benzyl bromide, 4,5-bis(bromomethyl)phenanthrene, 3-(bromomethyl) benzyltriphenylphosphonium bromide, 4-(bromomethyl) benzyltriphenylphosphonium bromide, 2-(bromomethyl) benzyltriphenylphosphonium bromide, 1-(2-bromoethyl)-2-(bromomethyl)-4-nitrobenzene, 2-bromo-5-fluorobenzylbromide, 2,6-bis(bromomethyl) fluorobenzene, o-bromomethylbenzoyl bromide, p-bromomethyl benzoyl bromide, 1-bromo-2-(bromomethyl)naphthalene, 2-bromo-5-methoxybenzyl bromide, 2,4-dichlorobenzyl chloride, 3,4-dichlorobenzyl chloride, 2,6-dichlorobenzyl chloride, 2,3-dichlorobenzyl chloride, 2,5-dichlorobenzyl chloride, methyldichlorosilyl(chloromethylphenyl)ethane, methyldichlorosilyl(chloromethylphenyl)ethane, methyldichlorosilyl(chloromethylphenyl)ethane, 3,5-dichlorobenzyl chloride, 3,5-dibromo-2-hydroxybenzyl bromide, 3,5-dibromobenzyl bromide, p-(chloromethyl) phenyltrichlorosilane, 1-trichlorosilyl-2-(p,m-chloromethylphenyl)ethane, 1-trichlorosilyl-2-(p,m-chloromethylphenyl)ethane, 1,2,4,5-tetrakis (bromomethyl) benzene. The term arylthioalkyl means an aryl group as attached to an alkyl group via an thioether sulfur atom, e.g., Ar—S—CH$_2$—. The term aralkoxycarbonyl means an aralkoxyl group attached to a carbonyl. Carbobenzoxy is an example of aralkoxycarbonyl. The term "heterocyclic ring system" means a saturated or partially unsaturated monocyclic, bicyclic or tricyclic heterocycle which contains one or more hetero atoms as ring atoms, selected from nitrogen, oxygen, silicon and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of aryl. Examples of such heterocyclic groups are pyrrolidinyl, piperidinyl, piperazinyl, morpholinyl, thiamorpholinyl, pyrrolyl, phthalimide, succinimide, maleimide, and the like. Also included are heterocycles containing two silicon atoms simultaneously attached to the nitrogen and joined by carbon atoms. The term "alkylamino" alone or in combination, means an amino-substituted alkyl group wherein the amino group can be a primary, or secondary amino group containing substituents selected from hydrogen, and alkyl, aryl, aralkyl, cycloalkyl, cycloalkylalkyl radicals and the like. The term "halogen" means fluorine, chlorine, bromine or iodine. The term dihaloalkyl means two halogen atoms, the same or different, substituted on the same carbon atom. The term "oxidizing agent" includes a single agent or a mixture of oxidizing reagents. Examples of mixtures of oxidizing reagents include sulfur trioxide-pyridine/dimethylsulfoxide, oxalyl chloride/dimethyl sulfoxide, acetyl chloride/dimethyl sulfoxide, acetyl anhydride/dimethyl sulfoxide, trifluoroacetyl chloride/dimethyl sulfoxide, toluenesulfonyl bromide/dimethyl sulfoxide, phosphorous pentachloride/dimethyl sulfoxide and isobutylchloroformate/dimethyl sulfoxide.

A general Scheme for the preparation of amino epoxides, useful as intermediates in the synthesis of HIV protease inhibitors is shown in Scheme 1 below.

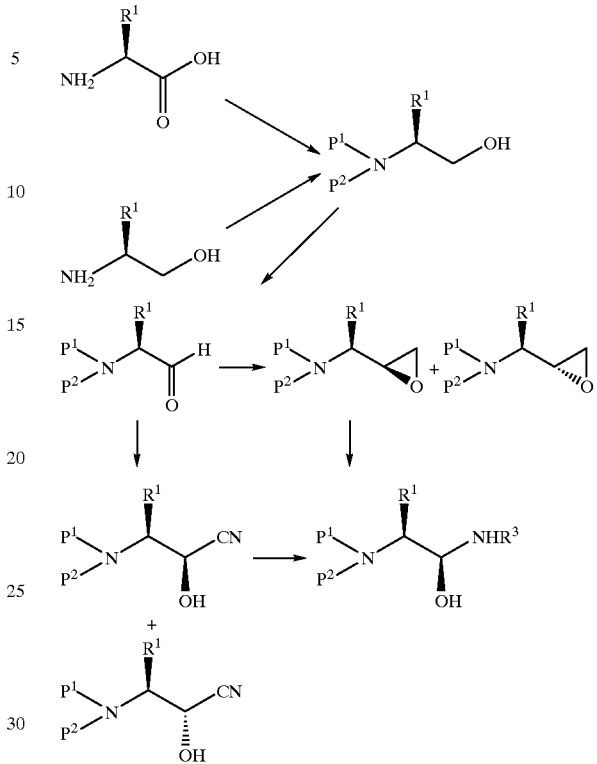

Scheme I

The economical and safe large scale method of preparation of protease inhibitors of the present invention can alternatively utilize amino acids or amino alcohols to form N,N-protected alpha-aminoalcohol of the formula

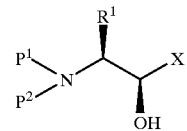

(II)

wherein $P^1$, $P^2$ and $R^1$ are described above.

Whether the compounds of Formula II are formed from amino acids or aminoalcohols, such compounds have the amine protected with groups $P^1$ and $P^2$ as previously identified. The nitrogen atom can be alkylated such as by the addition of suitable alkylating agents in an appropriate solvent in the presence of base.

Alternate bases used in alkylation include sodium hydroxide, sodium bicarbonate, potassium hydroxide, lithium hydroxide, potassium carbonate, sodium carbonate, cesium hydroxide, magnesium hydroxide, calcium hydroxide or calcium oxide, or tertiary amine bases such as triethyl amine, diisopropylethylamine, N-methylpiperidine, pyridine, dimethylaminopyridine and azabicyclononane. Reactions can be homogenous or heterogenous. Suitable solvents are water and protic solvents or solvents miscible with water, such as methanol, ethanol, isopropyl alcohol, tetrahydrofuran and the like, with or without added water. Dipolar aprotic solvents may also be used with or without added protic solvents including water. Examples of dipolar aprotic solvents include acetonitrile, dimethylformamide, dimethyl acetamide, acetamide, tetramethyl urea and its cyclic analog, dimethylsulfoxide, N-methylpyrrolidone, sulfolane, nitromethane and the like. Reaction temperature can range between about −20° to 100° C. with the preferred temperature of about 25–85° C. The reaction may be carried out under an inert atmosphere such as nitrogen or argon, or normal or dry air, under atmospheric pressure or in a sealed reaction vessel under positive pressure. The most preferred alkylating agents are benzyl bromide or benzyl chloride or monosubstituted aralkyl halides or polysubstituted aralkyl halides such as 2,6-dichlorobenzyl chloride. Sulfate or sulfonate esters are also suitable reagents to provide the corresponding benzyl analogs and they can be preformed from the corresponding benzyl alcohol or formed in situ by methods well known to those skilled in the art. Trityl, benzhydryl, substituted trityl and substituted benzhydryl groups, independently, are also effective amine protecting groups [$P^1,P^2$] as are allyl and substituted allyl groups. Their halide derivatives can also be prepared from the corresponding alcohols by methods well known to those skilled in the art such as treatment with thionyl chloride or bromide or with phosphorus tri- or pentachloride, bromide or iodide or the corresponding phosphoryl trihalide. Examples of groups that can be substituted on the aryl ring include alkyl, alkoxy, hydroxy, nitro, halo and alkylene, amino, mono- and dialkyl amino and acyl amino, acyl and water solubilizing groups such as phosphonium salts and ammonium salts. The aryl ring can be derived from, for example, benzene, napthelene, indane, anthracene, 9-(9-phenyl fluorenyl, durene, phenanthrene and the like. In addition, 1,2-bis (substituted alkylene) aryl halides or sulfonate esters can be used to form a nitrogen containing aryl or non-aromatic heterocyclic derivative [with $P^1$ and $P^2$] or bis-heterocycles. Cycloalkylenealkyl or substituted cycloalkylene radicals containing 6–10 carbon atoms and alkylene radicals constitute additional acceptable class of substituents on nitrogen prepared as outlined above including, for example, cyclohexylenemethylene.

Compounds of Formula II can also be prepared by reductive alkylation by, for example, compounds and intermediates formed from the addition of an aldehyde with the amine and a reducing agent, reduction of a Schiff Base, carbinolamine or enamine or reduction of an acylated amine derivative. Reducing agents include metals [platinum, palladium, palladium hydroxide, palladium on carbon, platinum oxide, rhodium and the like] with hydrogen gas or hydrogen transfer molecules such as cyclohexene or cyclohexadiene or hydride agents such as lithium aluminumhydride, sodium borohydride, lithium borohydride, sodium cyanoborohydride, diisobutylaluminum hydride or lithium tri-tert-butoxyaluminum hydride.

Additives such as sodium or potassium bromide, sodium or potassium iodide can catalyze or accelerate the rate of amine alkylation, especially when benzyl chloride was used as the nitrogen alkylating agent.

Phase transfer catalysis wherein the amine to be protected and the nitrogen alkylating agent are reacted with base in a solvent mixture in the presence of a phase transfer reagent, catalyst or promoter is another method of alkylating an amine nitrogen. The mixture can consist of, for example, toluene, benzene, ethylene dichloride, cyclohexane, methylene chloride or the like with water or a aqueous solution of an organic water miscible solvent such as THF. Examples of phase transfer catalysts or reagents include tetrabutylammonium chloride or iodide or bromide, tetrabutylammonium hydroxide, tri-butyloctylammonium chloride, dodecyltrihexylammonium hydroxide, methyltrihexylammonium chloride and the like.

A preferred method of forming substituted amines involves the aqueous addition of about 3 moles of organic halide to an amino acid or about 2 moles to an aminoalcohol. In a more preferred method of forming a protected amino alcohol, about 2 moles of benzylhalide in a basic aqueous solution is utilized. In an even more preferred method, the alkylation occurs at 50° C. to 80° C. with potassium carbonate in water, ethanol/water or denatured ethanol/water. In a more preferred method of forming a protected amino acid ester, about 3 moles of benzylhalide is added to a solution containing the amino acid.

The protected amino acid ester is additionally reduced to the protected amino alcohol in an organic solvent. Preferred reducing agents include lithium aluminiumhydride, lithium borohydride, sodium borohydride, borane, lithium tri-tert-butoxyaluminum hydride, borane·THF complex. Most preferably, the reducing agent is diisobutylaluminum hydride (DiBAL-H) in toluene. These reduction conditions provide an alternative to a lithium aluminum hydride reduction.

Purification by chromatography is possible. In the preferred purification method the alpha amino alcohol can be purified by an acid quench of the reaction, such as with hydrochloric acid, and the resulting salt can be filtered off as a solid and the amino alcohol can be liberated such as by acid/base extraction.

The protected alpha amino alcohol is oxidized to form a chiral amino aldehyde of the formula

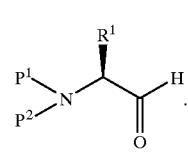

(III)

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydrothiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutylchloroformate and DMSO. The oxidation conditions reported by Reetz et al [Angew Chem., 99, p. 1186, (1987)], Angew Chem. Int. Ed. Engl., 26, p. 1141, 1987) employed oxalyl chloride and DMSO at −78° C.

The preferred oxidation method described in this invention uses sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminates and large scale operations are made less hazardous. Reaction at room temperature also eliminated the need for the use of low temperature reactor which makes the process more suitable for commercial production.

The reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either $P^1$ or $P^2$=H] or N,N-disubstituted aldehyde.

In addition, hydride reduction of an amide or ester derivative of the corresponding alkyl, benzyl or cycloalkenyl nitrogen protected phenylalanine, substituted phenylalanine or cycloalkyl analog of phenyalanine derivative can be carried out to provide a compound of Formula III. Hydride transfer is an additional method of aldehyde synthesis under conditions where aldehyde condensations are avoided, cf, Oppenauer Oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −20° C. to about 45° C., and preferably from abut 5° C. to about 25° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

An important aspect of the present invention is a reaction involving the addition of chloromethyllithium or bromomethyllithium to the alpha-amino aldehyde. Although addition of chloromethyllithium or bromomethyllithium to aldehydes is known, the essentially continuous in situ synthesis and accompanying addition of such species to racemic or chiral amino aldehydes under the conditions described hereafter to form aminoepoxides of the formula

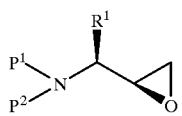

(IV)

is novel. The addition of chloromethyllithium or bromomethyllithium to a chiral amino aldehyde by this process is highly diastereoselective. The chloromethyllithium or bromomethyllithium is generated in-situ from the reaction of a dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane (DME), ethylene dichloride (EDC), methylene chloride (ME) or tert-butylmethylether (TBME) can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometallic reagents such as methyl lithium, tert-butyl lithium, sec-butyl lithium, phenyl lithium, phenyl sodium and the like. The organometallic reagents are usually used as solutions in solvents such as hexane, toluene and the like. Lithium metal have also been used to generate the halomethyllithium reagent. It can be added as received or pretreated or activated with, for example, a solvent, lithium naphtalide, ultrasound, scratching, grinding, degreasing and/or removing lithium hydroxide. The halomethylene generation in accordance with the present invention can be carried out at temperatures of between about −80° C. to 0° C. but preferably between about −60° C. to −10° C. The most preferred reaction temperatures are between −40° C. to −15° C. Reagents can be added singly or at the same time as will be discussed below. The preferred pressure of the reaction is atmospheric however a positive pressure is valuable under certain conditions such as a high humidity environment. A negative pressure can be used and can be useful, for example, for moving reagents, reaction mixtures or solutions from one vessel to another or between addition systems. The atmosphere of the reaction is usually an inert gas or gas mixture such as nitrogen, helium or argon.

The addition of n-butyl lithium to the dihalomethane, such as $BrCH_2Cl$, and aldehyde (III) solution is an extremely exothermic reaction. In the case of a batch or stepwise addition system as described in the prior art, the n-BuLi addition rate is limited by, for example, the ability of the cooling system to maintain a constant temperature and avoid hot spots. As a result, stepwise addition of, for example, n-butyl lithium to the other reagents, is practiced and the process requires frequent, tedious relatively small additions of this reagent. For multikilogram preparations, the total addition time could extend over 24 hours. The use of lithium metal requires preparing and handling a solid. Addition of a solid metal to a halide reagent can require frequent openings and closings of reaction vessels, generation of heat and hot spots in the reaction vessel or reaction solution and on the surface of the metal, thus causing rate differences between batches and/or individual addition steps. These variables and difficulties can apply or occur across or between preparations (batches) or within the same preparation or batch. It is also virtually impossible to supply exactly the proper number of chemical equivalents of pure metal to react completely and exactly with a haloalkyl or dihaloalkyl reagent. As a rule, these factors can make the metal reagent system inconvenient, expensive and a safety hazard especially in a large scale system. The novel continuous in situ synthesis process of the present invention provides epoxide (IV) in an improved or at least comparable yield consistently with safety and operational simplicity. The process also permits more efficient, and therefore reduced use of these expensive reagents.

An example of an arrangement for implementing the continuous in situ synthesis process of the present invention involves a Reactor A which can be agitated with or without a controlled atmosphere and/or maintained at room temperature, cooled or heated as desired. From Reactor A, a reagent or reagents with or without solvent (preferably the aldehyde (III) with a small amount of the dihalomethane reagent) can be pumped (mechanical, gas pressure differential or gravity) or siphoned into a mixing zone comprising a Mixer B or comprising a Mixer B and a Mixer B' which is substantially the same as Mixer B and connected as is Mixer B to Reactor A. Mixer B and Mixer B' can be interconnected or interact in series or in parallel. Mixer B and/or B' can be maintained at a low, high or room temperature, have a controlled atmosphere, can contain provisions for increasing mixing by mechanical means such as paddles or vanes such as those used in Morton Flasks, provide for static mixing via the reagent input systems, provide for mechanical mixing or stirring systems or a combination of methods as desired. The Mixers may also be equipped with a method or device such as discussed above for Reactor A that allows the addition of a new reagent or reagents and/or an additional amount of a previously or presently used reagent or mixture of reagents directly into the Mixers. The output from Mixer B and/or Mixer B' is transferred by any of the means discussed above into a Reactor B. Reactor B can be equipped as is Reactor A, for example, to heat or cool the reaction mixture and be equipped for the addition of reagents or solvents as required for continuation of a chemical synthesis or for work-up of a chemical syntheses reaction to provide the desired intermediate or final product.

There are several methods of implementing the continuous in situ synthesis process for preparing epoxide IV. For example, an organometallic reagent can be continuously added to a mixture of dihalomethane and aldehyde III, an organometallic reagent can be continuously added and, independantly, a dihalomethane can be continuously added to an aldehyde III, an organometallic reagent can be continuously added and additional dihalomethane can be continuously added to a mixture of dihalomethane and an aldehyde III, a mixture of an organometallic reagent and a dihalomethane can be continuously added to an aldehyde III, separate streams of an organometallic reagent, a dihalomethane and an aldehyde can be continuously mixed using one mixer or an organometallic reagent and a dihalomethane and an aldehyde can be continuously mixed using two mixers. As noted previously, preferably the aldehyde is primed with at least a portion of the dihalomethane reagent and then the organometallic reagent is continuously added, generally with the simultaneous addition of additional dihalomethane, for the continuous in situ synthesis of the halomethyllithium reagent. Rather than use a preformed organometallic reagent a mixture of a metal and a organic halide also can be used. An example of such is the use of n-butyl bromide and lithium metal. A preferred process for implementing the present invention involves the continuous mixing of an organometallic reagent, e.g., n-butyl lithium, with a preformed mixture of aldehyde III and dihalomethane. Other permutations will be recognized by those skilled in the art.

Alternative methods of conversion to the epoxides of this invention include substitution of other charged methylenation precurser species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of Formula III into their epoxide derivative have also been carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides form, using the preferred conditions of the invention, diastereoselectively in ratio amounts of at least about an 85:15 ratio (S:R). The product can be purified by chromatography to give the diastereomerically and enantiomerically pure product but the product is more conveniently used directly, without purification, to prepare HIV protease inhibitors.

The epoxide is then reacted, in a suitable solvent system, with an equal amount, or preferably an excess of, an amine ($R^3NH_2$) to form the amino alcohol of Formula I

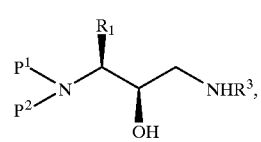

(I)

wherein $R^3$ is as defined above.

The reaction can be conducted over a wide range of temperatures, e.g., from about 10° C. to about 100° C., but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. In some cases, the amine ($R^3NH_2$) itself can be used as the solvent, such as isobutylamine.

Alternatively, the protected amino aldehyde of Formula III can also be reacted with a cyanide salt, such as sodium cyanide or potassium cyanide to form a chiral cyanohydrin of the formula

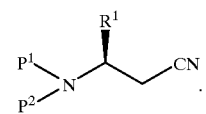

Preferably, a reaction rate enhancer, such as sodium bisulfite, is used to enhance the rate of cyanohydrin formation. Alternatively, trimethylsilylnitrile can be used to form a trimethylsilyloxycyano intermediate, which can be readily hydrolized to the cyanohydrin.

The reaction can be carried out at temperatures of between about –5° C. to 5° C. but preferably between about 0° C. to 5° C. The desired cyanohydrins form, using sodium cyanide and sodium bisulfite, diastereoselectively in ratio amounts of at least about an 88:12 ratio (S:R). The product can be purified by chromatography to give the diastereomerically and enantiomerically pure product.

The cyano group can be reduced to the amine of Formula V

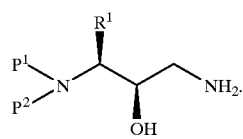

(V)

The reduction can be accomplished using a variety of reducing reagents, such as hydride transfer, metal reductions and catalytic hydrogenation which are well known to those skilled in the art. Examples of hydride reagents with and without heavy metal(s) or heavy metal salts as adjunct reagents include, for example, lithium aluminum hydride, lithium tri-tert-butoxyaluminum hydride, lithium trimethoxy-aluminum hydride, aluminum hydride, diborane (or borane), borane/THF, borane/dimethyl sulfide, borane/pyridine, sodium borohydride, lithium borohydride, sodium borohydride/cobalt salts, sodium borohydride/Raney-nickel, sodium borohydride/acetic acid and the like. Solvents for the reaction include, for the more reactive hydrides, THF, diethyl ether, dimethoxy ethane, diglyme, toluene, heptane, cyclohexane, methyl tert-butyl ether and the like. Solvents or solvent mixtures for reductions using reagents such as sodium borohydride, in addition to the non-protic solvents listed above, can include ethanol, n-butanol, tert-butyl alcohol, ethylene glycol and the like. Metal reductions include, for example, sodium and ethanol. Reaction temperatures can vary between solvent reflux and −20° C. An inert atmosphere such as nitrogen or argon is usually preferred especially where the possibility of flammable gas or solvent production/evolution is possible. Catalytic hydrogenation (metal catalyst plus hydrogen gas) can be carried out in the same solvents as above with metals or metal salts such a nickel, palladium chloride, platinum, rhodium, platinum oxide or palladium on carbon or other catalysts known to those skilled in the art. These catalysts can also be modified with, for example, phosphine ligands, sulfur or sulfur containing compounds or amines such as quinoline. Hydrogenations can be carried out at atmospheric pressure or at elevated pressures to about 1500 psi at temperatures between 0° to about 250° C. The most preferred reducing reagent is diborane-tetrahydrofuran, preferably at room temperature under an atmosphere of nitrogen and atmospheric pressure.

The amine of Formula V can then be reacted with $R^3L$, wherein L is a leaving group selected from halo, tosylate, and the like, and $R^3$ represents alkyl, alkenyl, alkynyl, hydroxyalkyl, alkoxyalkyl, cycloalkyl, cycloalkylalkyl, heterocycloalkyl, heterocycloalkylalkyl, aralkyl, and heteroaralkyl. Alternatively, the primary amino group of Formula V can be reductively alkylated with an aldehyde to introduce the $R^3$ group. For example, when $R^3$ is an isobutyl group, treatment of Formula V with isobutyraldehyde under reductive amination conditions affords the desired Formula I. Similarly, when $R^3$ is an isoamyl group, treatment of Formula V with isovaleraldehyde under reductive amination conditions affords the desired Formula I. Other aldehydes can be used to introduce various $R^3$ groups. Reductive amination can be performed using a variety of reaction conditions well-known to those skilled in the art. For example, the reductive amination of Formula V with an aldehyde can be carried out with a reducing agent such as sodium cyanoborohydride or sodium borohydride in a suitable solvent, such as methanol, ethanol, tetrahydrofuran and the like. Alternatively, the reductive amination can be carried out using hydrogen in the presence of a catalyst such as palladium or platinum, palladium on carbon or platinum on carbon, or various other metal catalysts known to those skilled in the art, in a suitable solvent such as methanol, ethanol, tetrahydrofuran, ethyl acetate, toluene and the like.

Alternatively, the amine of Formula I can be prepared by reduction of the protected amino acid of the following formula

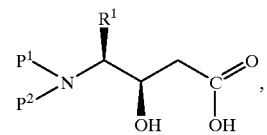

(commercially available from Nippon Kayaku, Japan) to the corresponding alcohol of formula

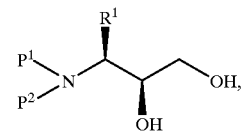

The reduction can be accomplished using a variety of reducing reagents and conditions. A preferred reducing reagent is diborane-tetrahydrofuran. The alcohol is then converted into a leaving group (L') by tosylation, mesylation or conversion into a halo group, such as chloro or bromo:

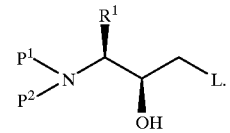

Finally, the leaving group (L') is reacted with $R^3NH_2$ as described above to form amino alcohol of Formula I. Alternatively, base treatment of the alcohol can result in the formation of the amino epoxide of Formula IV. A valuable intermediate in this process is the metal salt of the alcohol

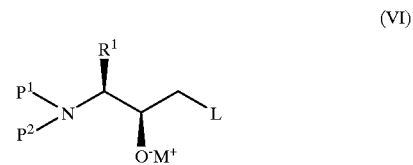

(VI)

shown in structure VI. The preferred metal M+ is lithium when the salt is formed under anhydrous conditions but sodium and potassium are satisfactory. Any of these salts and well as quaternary ammonium salts are satisfactory when the reaction is carried out under conditions wherein a protic solvent or co-solvent is used. The term protic solvent includes water. The metal may also be a di-charged species such as can be derived from calcium, magnesium, copper and the like. It should be noted that structure VI is also believed to be an intermediate in the continuous process of halomethyl lithium reagent formation and reaction with an aldehyde discussed below.

The above preparation of amino alcohol of Formula I is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at an intermediate or final step. Chiral auxiliaries such as one or two equivalents of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

A further advantage of the present process is that materials can be carried through the above steps without purification of the intermediate products. However, if purification is desired, the intermediates disclosed can be prepared and stored in a pure state.

The practical and efficient synthesis described here has been successfully scaled up to prepare large quantity of intermediates for the preparation of HIV protease inhibitors. It offers several advantages for multikilogram preparations: (1) it does not require the use of hazardous reagents such as diazomethane, (2) purification by chromatography is not required but can be used, (3) it is quick and efficient, (4) it utilizes inexpensive and readily available commercial reagents and (5) it produces alpha amino epoxides with satisfactory enantiomeric purity. In particular, the process of the invention produces enantiomerically clean epoxide as required for the preparation of enantiomerically clean intermediate for further synthesis of HIV protease inhibitors. It also is expected that the present invention permits more efficient use of the dihalomethane and organometallic reagents relative to the stepwise addition process of the prior art.

The novel continuous in situ synthesis process has several additional advantages that are especially valuable when applied to large scale multikilogram preparations. It eliminates the frequent batch addition of reagents thus demanding less chemist time. It also requires less time monitoring the reaction(s). In the continuous in situ synthesis process of this invention, temperature control of the reaction vessel or vessels (mixers) wherein reagent mixing occurs is much easier and less expensive since smaller containers are required. Large, expensive low-temperature reactors are not required due to rapid, continuous, flow through of the aldehyde (III) and the in situ generated halomethyl lithium reagent. Improvements in temperature control also allows additional choices regarding temperatures and rate.

The amino epoxides were prepared utilizing the following procedure as disclosed in Scheme II below.

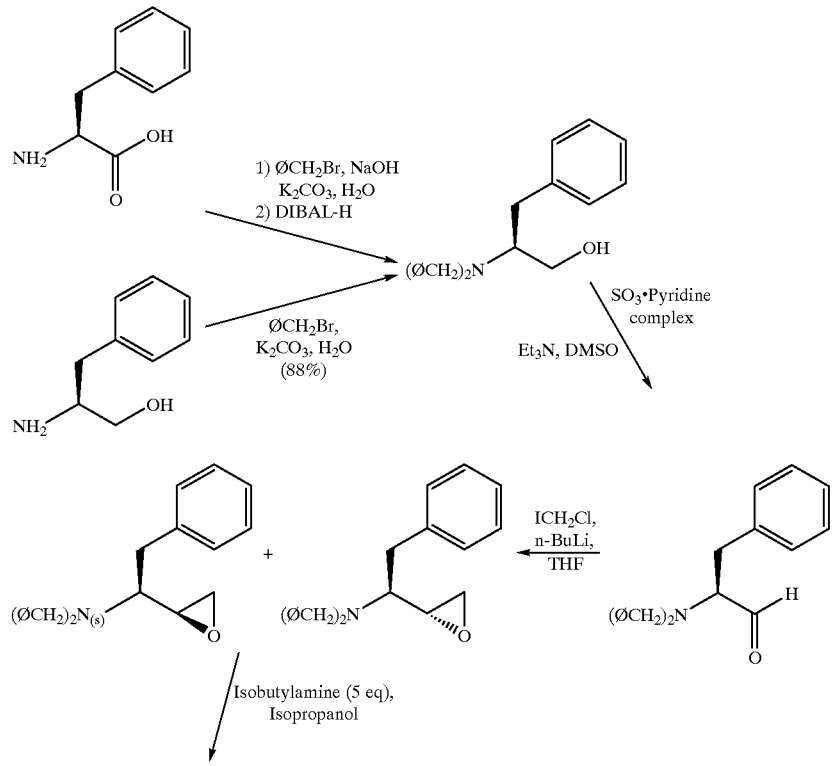

Scheme II

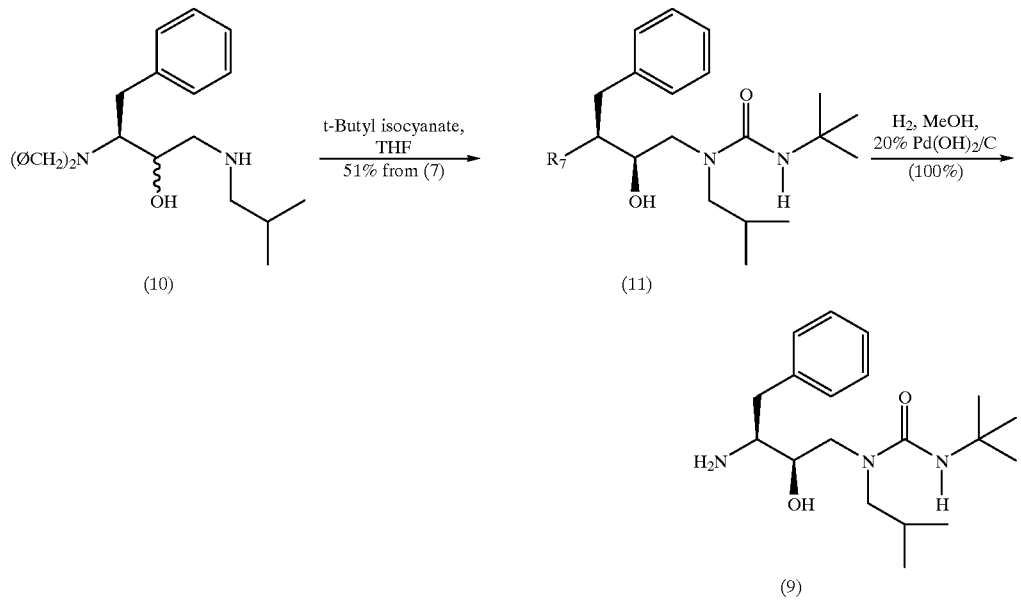

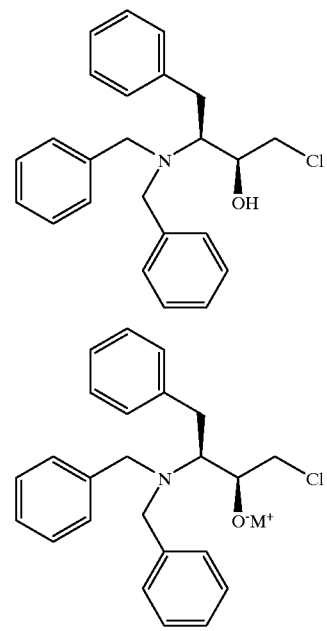

In Scheme II, there is shown a synthesis for the epoxide, chiral N,N,α-S-tris(phenylmethyl)-2S-oxiranemethanamine. The synthesis starts from L-phenylalanine. The aldehyde is prepared in three steps from L-phenylalanine or phenylalinol. L-Phenylalanine is converted to the N,N-dibenzylamino acid benzyl ester using benzyl bromide under aqueous conditions. The reduction of benzyl ester is carried out using diisobutylaluminum hydride (DIBAL-H) in toluene. Instead of purification by chromatography, the product is purified by an acid (hydrochloric acid) quench of the reaction, the hydrochloride salt is filtered off as a white solid and then liberated by an acid/base extraction. After one recrystallization, chemically and optically pure alcohol is obtained. Alternately, and preferably, the alcohol can be obtained in one step in 88% yield by the benzylation of L-phenylalaninol using benzyl-bromide under aqueous conditions. The oxidation of alcohol to aldehyde is also modified to allow for more convenient operation during scaleup. Instead of the standard Swern procedures using oxalyl chloride and DMSO in methylene chloride at low temperatures (very exothermic reaction), sulfur trioxide-pyridine/DMSO was employed (Parikh, J., Doering, W., J. Am. Chem. Soc., 89, p. 5505, 1967) which can be conveniently performed at room temperature to give excellent yields of the desired aldehyde with high chemical and enantiomer purity which does not require purification.

In the present invention, chloromethyllithium or bromomethyllithium is generated in-situ from chloroiodomethane (or bromochloromethane) or dibromomethane and n-butyllithium at a temperature in a range from about –80° C. to about –0° C. in THF in the presence of aldehyde. Preferred temperatures are between –60° C. to –10° C. The most preferred reaction temperatures are between –40° C. to –15° C. The products of this reaction are believed to be the chlorohydrin and/or its lithium salt as shown above. The metal salt is the initial product and intermediate from the addition of the halomethyl organometallic reagent to the aldehyde. It is also an intermediate in the transformation of the halohydrin into the epoxide. The desired chlorohydrin or bromohydrin is formed as evidenced by TLC analyses. After warming to room temperature, the desired epoxide is formed diastereoselectively in a 85:15 ratio (S:R). The product can be purified by chromatography to give the diastereomerically pure product as a colorless oil but it is more conveniently used directly without purification.

Scheme II also shows an example of the preparation of a valuable urea such as compound (9). The same intermediate

(10) can be used in a like manner to prepare novel and valuable sulfonamides such as shown in Example 33.
Scheme III illustrates the preparation of the aminopropy-lurea (9) utilizing mixed protected amine of phenylalaninol, where BOC is t-butoxycarbonyl and Bn is benzyl.
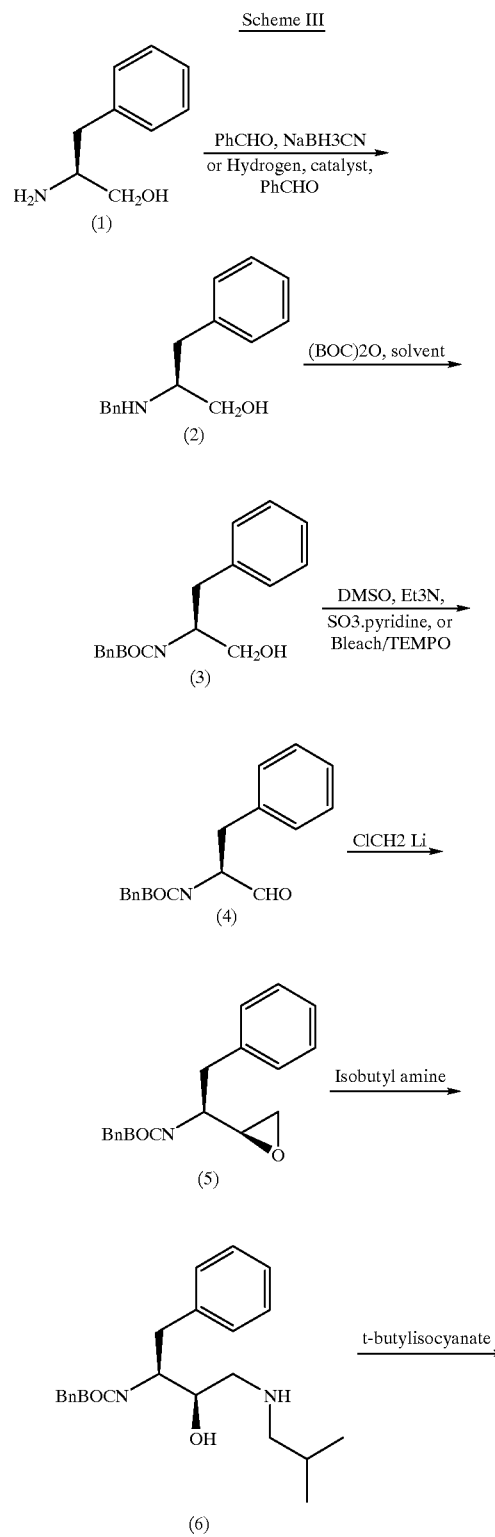
Scheme IV illustrates an alternative preparation of the amino epoxide (5) utilizing a sulfur ylide.
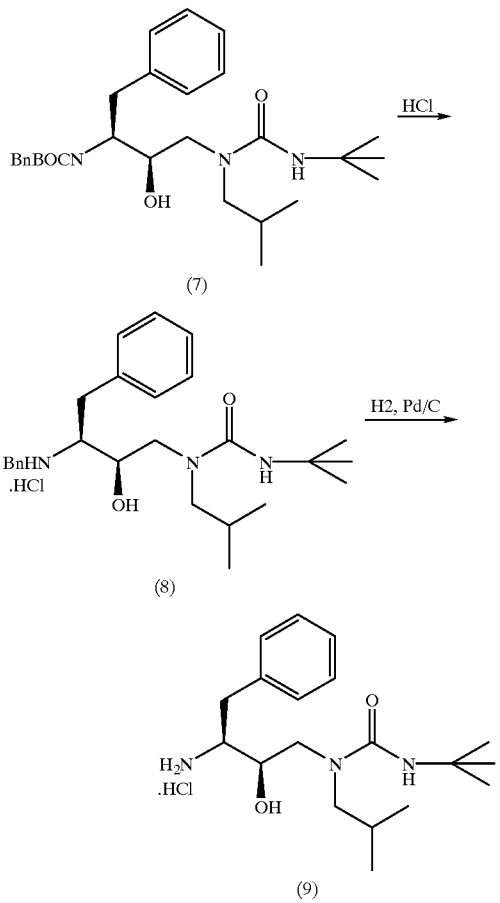
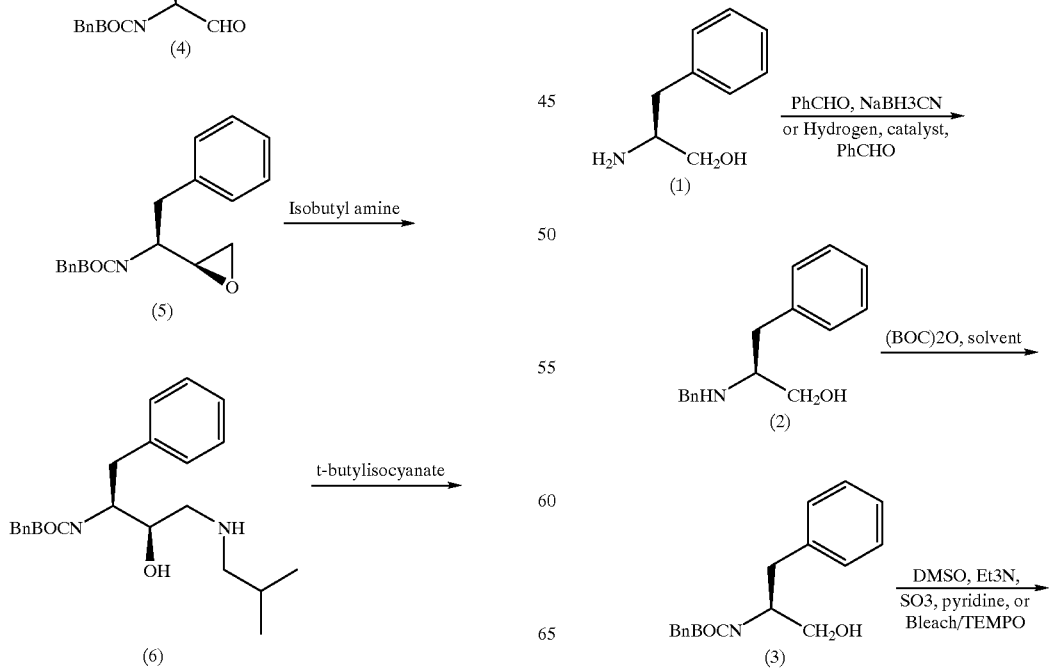

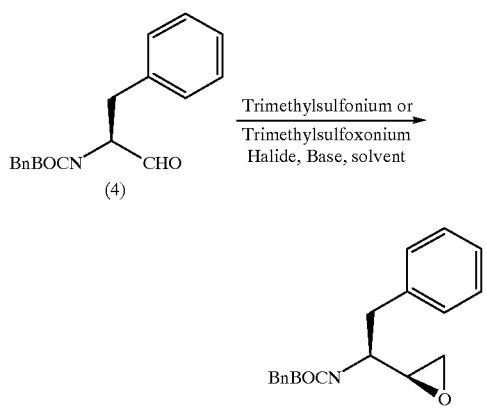

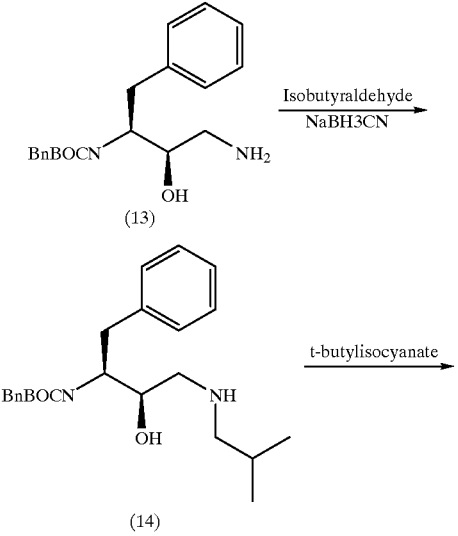

The aminopropylurea (9) was also prepared utilizing the procedure as disclosed in Scheme V below.

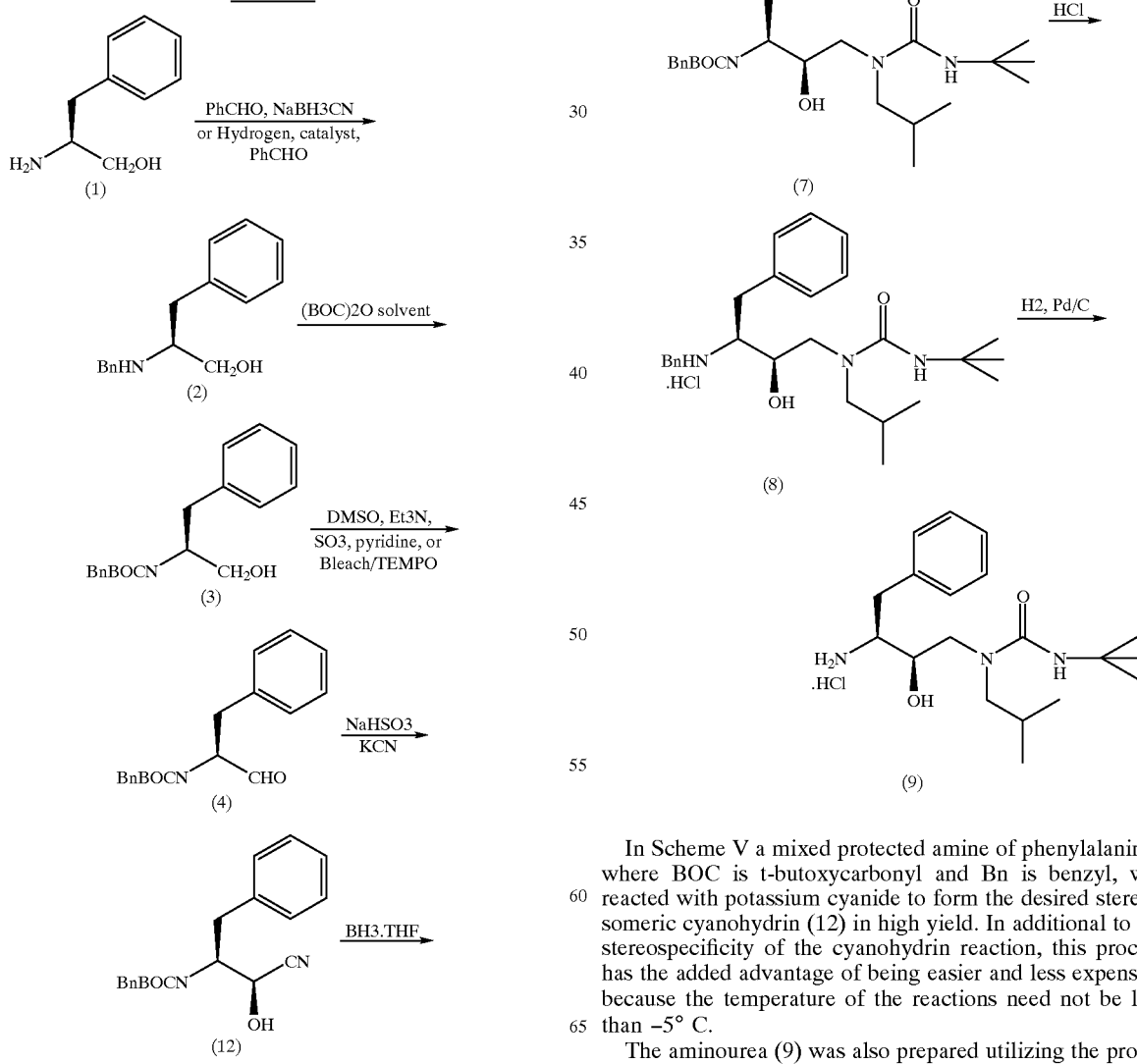

In Scheme V a mixed protected amine of phenylalaninal, where BOC is t-butoxycarbonyl and Bn is benzyl, was reacted with potassium cyanide to form the desired stereoisomeric cyanohydrin (12) in high yield. In additional to the stereospecificity of the cyanohydrin reaction, this process has the added advantage of being easier and less expensive because the temperature of the reactions need not be less than −5° C.

The aminourea (9) was also prepared utilizing the procedure as disclosed in Scheme VI below.

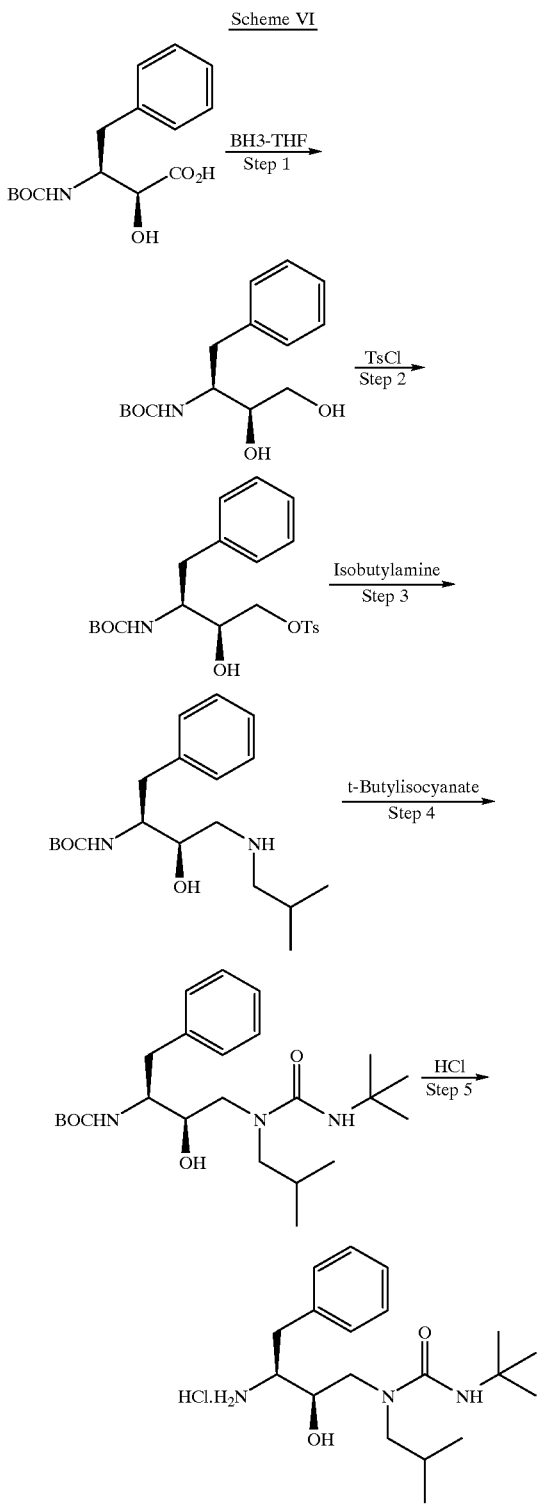

Scheme VI

The procedure in Scheme VI required only one protecting group, BOC, for the amine of the hydroxyamino acid. This procedure has the advantage of having the desired stereochemistry of the benzyl and hydroxy groups established in the starting material. Thus the chirality does not need to be introduced with the resulting loss of material due to preparation of diastereomers.

The Schemes above illustrate reaction of a substituted 1-amino-2-hydroxy-3-(protected)amino-4-substituted-butanediamines with an isocyanate to produce a urea as a key intermediate in the preparation of HIV-protease inhibitors. Treatment of, for example, the a substituted 1-amino-2-hydroxy-3-(protected)amino-4-substituted-butanediamines with a sulfonyl chloride will provide a key intermediate in the synthesis of sulfonamide HIV-protease inhibitors.

EXAMPLE 1

β-2-[Bis(phenylmethyl)amino]benzenepropanol

METHOD 1:

Step 1: Benzylation of L-Phenylalanine

A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time ~25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexanes). Usually the product is pure enough to be used directly in the next step without further purification. $^1$H NMR spectrum was in agreement with published literature. $^1$H NMR (CDCL$_3$) ∂, 3.00 and 3.14 (ABX-system, 2H, $J_{AB}$=14.1 Hz, $J_{AX}$=7.3 Hz and $J_{BX}$=5.9 Hz), 3.54 and 3.92 (AB-System, 4 H, $J_{AB}$=13.9 Hz), 3.71 (t, 1H, J=7.6 Hz), 5.11 and 5.23 (AB-System, 2H, $J_{AB}$=12.3 Hz), and 7.18 (m, 20 H). EIMS: m/z 434 (M-1).

Step 2: βS-2-[Bis(phenylmethyl)amino]benzenepropanol from the DIBAL Reduction of N,N-bis(phenylmethyl)-L-Phenylalanine phenylmethyl ester The benzylated phenylalanine phenylmethyl ester (0.302 mol) from the previous reaction was dissolved in toluene (750 mL) and cooled to −55° C. A 1.5 M solution of DIBAL in toluene (443.9 mL, 0.666 mol) was added at a rate to maintain the temperature between −55 to −50° C. (addition time ~1 hr). The mixture was stirred for 20 minutes under a nitrogen atmosphere and then quenched at −55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5 N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of βS-2-[Bis (phenylmethyl)amino]benzenepropanol, 40% yield from L-phenylalanine. An additional 7 g (7%) of product can be obtained from recrystallization of the concentrated mother liquor. TLC of product Rf=0.23 (10% ethyl acetate/hexane, silica gel); $^1$H NMR (CDCl$_3$) ∂ 2.44 (m, 1H,), 3.09 (m, 2H), 3.33 (m, 1H), 3.48 and 3.92 (AB-System, 4H, J$_{AB}$=13.3 Hz), 3.52 (m, 1H) and 7.23 (m, 15H); [α]$_D$25+42.4 (c 1.45, CH$_2$Cl$_2$); DSC 77.67° C.; Anal. Calcd.for C$_{23}$H$_{25}$ON: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

METHOD 2:

Preparation of βS-2-[Bis(Phenylmethyl)amino]Bezenepropanol from the N,N-Dibenzylation of L-Phenylalaninol:

L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnite to give a semi-dry solid (407 g) which was recrystallized from 1.1 L of ethyl acetate/heptane (1:10 by volume). The product was isolated by filtration (at −8° C. ), washed with 1.6 L of cold (−10° C.) ethyl acetate/heptane (1:10 by volume) and airdried to give 339 g (88% yield) of βS-2-[Bis (phenylmethyl)amino]benzene-propanol, mp 71.5–73.0° C. More product can be obtained from the mother liquor if necessary. The other analytical characterization was identical to compound prepared as described in Method 1.

EXAMPLE 2

αS-[Bis(phenylmethyl)amino] benzenepropanaldehyde

METHOD 1:

βS-2-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time ~1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenched with 1.6 L of cold water (10–15° C.) over 45 minutes. The resultant solution was extracted with ethyl acetate (2.0 L), washed with 5% citric acid (2.0 L), and brine (2.2 L), dried over MgSO$_4$ (280 g) and filtered. The solvent was removed on a rotary evaporator at 35–40° C. and then dried under vacuum to give 198.8 g of αS-[Bis-(phenylmethyl)amino]-benzenepropanaldehyde as a pale yellow oil (99.9%). The crude product obtained was pure enough to be used directly in the next step without purification. The analytical data of the compound were consistent with the published literature. [α]$_D$25=−92.9° (c 1.87, CH$_2$Cl$_2$); $^1$H NMR (400 MHz, CDCl$_3$) ∂, 2.94 and 3.15 (ABX-System, 2H, J$_{AB}$=13.9 Hz, J$_{AX}$=7.3 Hz and J$_{BX}$=6.2 Hz), 3.56 (t, 1H, 7.1 Hz), 3.69 and 3.82 (AB-System, 4H, J$_{AB}$=13.7 Hz), 7.25 (m, 15 H) and 9.72 (s, 1H); HRMS calcd for (M+1) C$_{23}$H$_{24}$NO 330.450, found: 330.1836. Anal. Calcd. for C$_{23}$H$_{23}$ON: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enanatiomer 10.62 min.

METHOD 2:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time ~1.25 hr). The mixture was stirred for 5 min. followed by addition of a solution of βS-2-[bis (phenylmethyl)amino]benzene-propanol (0.074 mol) in 100 ml of dichloromethane (addition time ~20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give αS-[bis(phenylmethyl)amino] benzenepropanaldehyde. The aldehyde was carried on to the next step without purification.

METHOD 3:

To a mixture of 1.0 g (3.0 mmoles) of βS-2-[bis (phenylmethyl)amino]benzenepropanol 0.531 g (4.53 mmoles) of N-methyl morpholine, 2.27 g of molecular sieves (4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of αS-2-[bis(phenylmethyl)amino]benzene propanaldehyde as a pale yellow oil.

METHOD 4:

To a solution of 1.0 g (3.02 mmoles) of βS-2-[bis (phenylmethyl)amino]benzenepropanol in 9.0 mL of toluene was added 4.69 mg (0.03 mmoles) of 2,2,6,6-tetramethyl-1-piperidinyloxy, free radical (TEMPO), 0.32 g (3.11 mmoles) of sodium bromide, 9.0 mL of ethyl acetate and 1.5 mL of water. The mixture was cooled to 0° C. and an aqueous solution of 2.87 mL of 5% household bleach containing 0.735 g (8.75 mmoles) of sodium bicarbonate and 8.53 mL of water was added slowly over 25 minutes. The mixture was stirred at 0° C. for 60 minutes. Two more additions (1.44 mL each) of bleach was added followed by stirring for 10 minutes. The two phase mixture was allowed to separate. The aqueous layer was extracted twice with 20 mL of ethyl acetate. The combined organic layer was washed with 4.0 mL of a solution containing 25 mg of potassium iodide and water (4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of the desired product aldehyde, αS-[bis(phenylmethyl)amino] benzenepropanaldehyde.

METHOD 5:

Following the same procedures as described in Example 2 (Method 1) except 3.0 equivalents of sulfur trioxide pyridine complex was used and αS-[bis(phenylmethyl) amino]benzenepropanaldehyde was isolated in comparable yields.

EXAMPLE 3

N,N,αS-Tris(phenylmethyl)-2S-oxiranemethanamine
METHOD 1:

A solution of αS-[Bis(phenylmethyl)amino] benzenepropanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyllithium (110 mL) at <−25° C. After addition the mixture was stirred at −30 to −35° C. for 10 minutes. This was repeated once. (2) Additional chloroiodomethane (8.5 mL, 0.11 mol) was added, followed by n-butyllithium (55 mL, 0.088 mol) at <−25° C. After addition the mixture was stirred at −30 to −35° C. for 10 minutes. This was repeated 5 times. (3) Additional chloroiodomethane (8.5 mL, 0.11 mol) was added, followed by n-butyllithium (37 mL, 0.059 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N,αS-Tris(phenylmethyl)-2S-oxiranemethanamine $^1$H NMR (400 MHz, CDCl$_3$) ∂ 2.49 and 2.51 (AB-System, 1H, J$_{AB}$=2.82), 2.76 and 2.77 (AB-System, 1H, J$_{AB}$=4.03), 2.83 (m, 2H), 2.99 & 3.03 (AB-System, 1H, J$_{AB}$=10.1 Hz), 3.15 (m, 1H), 3.73 & 3.84 (AB-System, 4H, J$_{AB}$=14.00), 7.21 (m, 15H); $^{13}$C NMR (400 MHz,CDCl$_3$) ∂ 139.55, 129.45, 128.42, 128.14, 128.09, 126.84, 125.97, 60.32, 54.23, 52.13, 45.99, 33.76; HRMS calcd for C$_{24}$H$_{26}$NO (M+1) 344.477, found 344.2003.

N,N,αS-Tris(phenylmethyl)-2R-oxiranemethanamine $^1$H NMR (300 MHz, CDCl$_3$) ∂ 2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of(8): 9.38 min., retention time of enanatiomer of (4): 13.75 min.

METHOD 2:

A solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyllithium in hexane (25 ml, 0.040 mol) was then added at a rate to maintain the temperature at −75° C. (addition time ~15 min.). After the first addition, additional chloroiodomethane (1.6 ml, 0.022 mol) was added again, followed by n-butyllithium (23 ml, 0.037 mol), keeping the temperature at −75° C. The mixture was stirred for 15 min. Each of the reagents, chloroiodomethane (0.70 ml, 0.010 mol) and n-butyllithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

METHOD 3:

A solution of αS-[Bis(phenylmethyl)amino]benzenepropanaldehyde (178.84 g, 0.54 mol) and bromochloromethane (46 mL, 0.71 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyllithium (102 mL) at <−25° C. After addition the mixture was stirred at −30 to −35° C. for 10 minutes. This was repeated once. (2) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

METHOD 4:

Following the same procedures as described in Example 3 (Method 3) except the reaction temperatures were at −20° C. The resulting N,N,αS-tris(phenylmethyl)-2S-oxiranemethanamine was a diastereomeric mixture of lesser purity then that of Method 3.

METHOD 5:

Following the same procedures as described in Example 3 (Method 3) except the reaction temperatures were at −70–78° C. The resulting N,N,αS-tris(phenylmethyl)-2S-oxiranemethanamine was a diastereomic mixture, which was used directly in the subsequent steps without purification.

METHOD 6:

Following the same procedures as described in Example 3 (Method 2) except dibromomethane was used instead of chloroiodomethane. After the reaction and work up procedures as described in Example 3 (Method 2), the desired N,N,αS-tris(phenylmethyl)-2S-oxirane-methanamine was isolated.

METHOD 7:

In a round bottom flask equipped with mechanical stirrer, thermometer, addition funnel was added THF (760 ml) followed by αS-[Bis(phenylmethyl)amino]benzene-propanaldehyde (76 g, 230.7 mmol) under nitrogen. The solution was then cooled to −30° C. and BrCH$_2$Cl (39.7 g, 306.8 mmol) was then charged into the reaction mixture. The solution was stirred for 5 min and the temperature was maintained at −35+/−5° C. In this experiment, n-butyl lithium addition was continuous with periodic additions of additional amounts of dihalomethane reagent. A first portion of n-BuLi (144 ml) was added to the reactor through an addition funnel. A small portion of BrCH$_2$Cl (6 ml) was quickly introduced into reaction mixture using syringe without stopping n-BuLi charging. After an additional 44 ml of n-BuLi (continuous addition) had been added into reaction mixture, another small portion of BrCH$_2$Cl (6 ml) was transferred into the reaction mixture in the same manner. After an additional 44 ml of n-BuLi was added into reaction mixture, again BrCH$_2$Cl (3 ml) was charged into reaction mixture and followed by 22 ml of n-BuLi. This addition sequence was repeated 7 times without interrupting n-BuLi charging. The reaction mixture was then warmed to room temperature and stirred for additional 4 hours. A small aliquot was then taken and checked by TLC for the epoxide formation completion. The reaction mixture was then quenched with 16% NH$_4$Cl$_{(aq)}$ (440 ml). After phase separation, the organic layer was condensed at 60° C. under reduced pressure to give 82.2 g of crude oil containing the desired N,N,αS-tris(phenylmethyl)-2S-oxirane-methanamine.

METHOD 8:

To a round bottom flask equipped with mechanical stirrer, thermometer, was added THF (220 ml) followed by αS-[Bis(phenylmethyl)amino]benzene-propanaldehyde (25 g, 75.9 mmol) under nitrogen. The solution was then cooled to −35° C. and BrCH$_2$Cl (5.7 ml, 87.7 mmol) was then charged into the reaction mixture. The solution was stirred for 5 min and the temperature was maintained at −35+/−5° C. Bromochloromethylene (BrCH$_2$Cl) (6.8 ml) and 1.6M n-BuLi (104.2 ml) were approximately simultaneously introduced into the reactor by syringe pumps with addition rates of 0.16 ml/min and 2.5 ml/min respectively. After the addition was completed, the reaction mixture was then warmed to room temperature and stirred 4 hours. The resulting reaction mixture was then quenched with 16% NH$_4$Cl$_{(aq)}$ (190 ml) and the resulting phases were separated. The organic layer was washed with water (190 ml) and then condensed under reduced pressure at 60° C. The residue oil was azeotroped with toluene (30 ml×2) to give 27.14 g of crude oil. The HPLC analysis showed 40.2 wt % of desired N,N,αS-tris (phenylmethyl)-2S-oxirane-methanamine (41.8% yield).

METHOD 9:

In a round bottom flask equipped with a mechanical stirrer, a Teflon outlet line, and a thermometer was added THF (500 ml) followed by αS-[Bis(phenylmethyl)amino] benzenepropanaldehyde (10 g, 30.4 mmol) under nitrogen. And then BrCH$_2$Cl (5 ml, 76.9 mmol) was charged into reactor and the solution was stirred for 5 min at room temperature. The Teflon outlet of reactor A was connected to a static mixer which was immersed in a cooling bath at a temperature of approximately −30° C. A separate flask equipped with a mechanical stirrer, a Teflon inlet line, and a thermometer was connected to the outlet of the static mixer. The aldehyde/BrCH$_2$Cl/THF solution in the first flask was pumped through the static mixer through the Teflon line at a speed of 21 ml/min. At the same time, the n-BuLi (1.6 M) (approximately 42 ml) was introduced into the static mixer by a syringe pump at a speed of 1.8 ml/min. The reaction mixture from the static mixer was stirred in the second reactor and warmed to room temperature immediately. After the chlorohydrin was converted into the epoxide, the reaction mixture was quenched with 16% NH$_4$Cl $_{(aq)}$ (150 ml). The organic layer was washed with H$_2$O (150 ml) and then concentrated. The residue was then azeotroped with toluene (100 ml) to give 11.06 g of brown crude N,N,αS-tris (phenylmethyl)-2S-oxirane-methanamine. The HPLC analysis indicated 52.3 wt % of desired epoxide N,N,αS-tris(phenylmethyl)-2S-oxirane-methanamine (55.48% yield).

EXAMPLE 3A

A solution of the aldehyde 3 (190 Kg; 576 mol) and chloroiodomethane (48.8 L; 751 mol) in tetrahydrofuran (1900 L) was cooled to −40 to −45° C. in a stainless steel reactor. A solution of n-butyllithium in hexane (1.6 M, 244 Kg) was then added at a rate that maintained the temperature below −30° C. After addition the mixture was stirred at −30 to −35° C. for 10 minutes. More additions of reagents were carried out in the following manner: (1) Additional chloroiodomethane (15.2 L) was added, followed by n-butyllithium (73.3 Kg) at <−30° C. After addition was complete, the mixture was stirred at −30 to −35° C. for 10 minutes. This was repeated three times. A sample was taken for in process control by HPLC. The chlorohydrin reaction is considered complete when the aldehyde content is less than 5%. The reaction mixture was warmed to ambient temp. and stirred at room temperature for at least 2 hours until HPLC or TLC (silica gel, 20% ethyl acetate/hexane) indicated that the epoxidation reaction was completed. The reaction mixture was cooled to 5° C. and quenched with 16% ammonium chloride solution (1092 L). After keeping stirring at the temperature below 25° C. for 30 min, the layers were separated. The organic phase was extracted with water (825 L). After phase separation, the organic phase was concentrated at 60° C. under vacuum until a minimum stirrable volume. Toluene (430 L) was then added to the reactor and evaporated to minimum stirrable volume. This procedure was then repeated twice to give brown oily residue 4 (The crude product weight was >100% yield). The composition of this crude oily product mixture was analyzed by HPLC (column, Partisil 5 (manufacturer, Whatman); 250 mm×4.6 mmi.d., 5 μm particle size; mobile phase, hexane/methyl tert-butyl ether, 95:5 (v/v); flow rate, 1.0 mL/min; UV detector at 215 nm; retention time of alcohol=6.5 min; retention time of undesired epoxide=9.5 min; retention time of desired epoxide=10.5 min). The crude product contained approximately 55% of the desired epoxide at this point. The optical purity of the product was determined to be >99.9%. The other analytical data such as NMR were consistent with the published literature. The oil obtained was used in next step without purification.

EXAMPLE 4

3S-[N,N-Bis(phenylmethyl)amino]-1-(2-methylpropyl)amino-4-phenylbutan-2R-ol

To a solution of crude N,N,αS-tris(phenylmethyl)-2S-oxiranemethanamine (388.5 g, 1.13 mol) from Example 3 in isopropanol (2.7 L) (or ethyl acetate) was added isobutylamine (1.7 kgm, 23.1 mol) over 2 min. The temperature increased from 25° C. to 30° C. The solution was heated to 82° C. and stirred at this temperature for 1.5 h. The warm solution was concentrated under reduced pressure at 65° C. The brown oil residue was transferred to a 3-L flask and dried in vacuo (0.8 mm Hg) for 16 h to give 450 g of 3S-[N,N-bis(phenylmethyl)amino]-1-(2-methylpropyl)amino-4-phenylbutan-2R-ol as a crude oil. The product was used directly in the next step without purification. An analytical sample of the desired major diastereomeric product was obtained by purifying a small sample of crude product by silica gel chromatography (40% ethyl acetate/hexane). Tlc analysis: silica gel, 40% ethyl acetate/hexane; Rf=0.28; HPLC analysis: ultrasphere ODS column, 25% triethylamine/phosphate buffer pH 3/acetonitrile, flow rate 1 mL/min, UV detector; retention time 7.49 min.; HRMS calcd for C28H37N2O (M+1) 417.616, found 417.2887.

An analytical sample of the minor diastereomeric product, 3S-[N,N-bis(phenylmethyl)amino]-1-(2-methylpropyl) amino-4-phenylbutan-2S-ol was also obtained by purifying a small sample of crude product by silica gel chromatography (40% ethyl acetate/hexane).

EXAMPLE 5

3S-[N,N-Bis(phenylmethyl)amino]-1-(3-methylbutyl)amino-4-phenylbutan-2R-ol

Example 4 was followed using isoamylamine instead of isobutylamine to prepare 3S-[N,N-Bis(phenylmethyl) amino]-1-(3-methylbutyl)amino-4-phenylbutan-2R-ol and 3S-[N,N-Bis(phenylmethyl)amino]-1-(3-methylbutyl) amino-4-phenylbutan-2S-ol in comparable yields to that of Example 4. The crude amine was used in the next step without further purification.

EXAMPLE 6

N-[3S-[N,N-Bis(phenylmethyl)amino]-2R-hydroxy-4-phenylbutyl]-N'-(1,1-dimethylethyl)-N-(2-methylpropyl)urea A solution of the crude 3S-[N,N-Bis(phenylmethyl) amino]-1-(2-methylpropyl)amino-4-phenylbutan-2R-ol (446.0 g, 1.1 mol) from Example 4 in tetrahydrofuran (6 L) (or ethyl acetate) was cooled to 8° C. t-Butyl isocyanate (109.5 g, 1.1 mol) was then added to the solution of the amine from an addition funnel at a rate that maintained the temperature between 10–12° C. (addition time was about 10 min). The external cooling was stopped and the reaction was warmed to 18° C. after 30 min. The solution was transferred directly from the reactor to a rotary evaporator flask (10 L) through a teflon tube using vacuum and then concentrated. The flask was heated in a 50° C. water bath during the 2 h required for the distillation of the solvent. The brown residue was dissolved in ethyl acetate (3 L), washed with 5% aq citric acid solution (1×1.2 L), water (2×500 mL), brine (1×400 mL), dried over magnesium sulfate (200 g) and filtered. The volume of product solution was reduced to 671 mL over 2 h on a rotary evaporator at 50° C. The concentrate was stirred and diluted with 1.6 L of hexane. The mixture was cooled to 12° C. and stirred for 15 hours. The product crystals were isolated by filtration, washed with 10% ethyl acetate/hexane (1×500 mL), hexane (1×200 mL) and dried in vacuo (2 mm) at 50° C. for 1 hour to give 248 g of N-[3S-[N,N-bis-(phenylmethyl)amino]-2R-hydroxy-4-phenylbutyl]-N'-(1,1-dimethylethyl)-N-(2-methylpropyl)-urea. The mother liquor and washes were combined and concentrated on a rotary evaporator to give 270 g of a brown oil. This material was dissolved in ethyl acetate (140 mL) at 50° C. and diluted with hexane (280 mL) and seeded with crystals of the first crop product (20 mg). The mixture was cooled in an ice bath and stirred for 1 h. The solid was isolated by filtration, washed with 10% ethyl acetate/hexane (1×200 mL) and dried in vacuo (2 mm) at 50° C. for 1 h to give 55.7 g of 11 as the second crop (49% overall yield). Mp 126° C.; [α]D25=−59.0° (c=1.0, CH2Cl2), TLC: Rf 0.31 (silica gel, 25% ethyl acetate/hexane).

An analytical sample of the minor diasatereomer, N-[3S-[N,N-bis(phenylmethyl)amino]-2S-hydroxy-4-phenylbutyl]-N'-(1,1-dimethylethyl)-N-(2-methylpropyl) urea was isolated by silica-gel chromatography (10–15% ethyl acetate/hexane) in an earlier experiment and characterized.

EXAMPLE 7

N-[3S-[N,N-Bis(phenylmethyl)amino]-2R-hydroxy-4-phenylbutyl]-N'-(1,1-dimethylethyl)-N-(3-methylbutyl)urea The crude product from Example 5 was reacted with t-butylisocyanate following the method of Example 6 to prepare N-[3S-[N,N-Bis(phenylmethyl)amino]-2R-hydroxy-4-phenylbutyl]-N'-(1,1-dimethylethyl)-N-(3-methylbutyl)urea and N-[3S-[N,N-Bis(phenylmethyl) amino]-2S-hydroxy-4-phenylbutyl]-N'-(1,1-dimethylethyl)-N-(3-methylbutyl)urea in comparable yields to that of Example 6.

EXAMPLE 8

N-[3S-Amino-2R-hydroxy-4-phenylbutyl]-N'-(1,1-dimethylethyl)-N-(2-methylpropyl)urea N-[3S-[N,N-Bis(phenylmethyl)amino]-2R-hydroxy-4-phenylbutyl]-N'-(1,1-dimethylethyl)-N-(2-methylpropyl) urea (125.77 g, 0.244 mol) from Example 6 was dissolved in ethanol (1.5 L) (or methanol) and 20% palladium hydroxide on carbon (18.87 g) (or 4% palladium on carbon) was added to the solution under nitrogen. The mixture was stirred at ambient temperature under a hydrogen atmosphere at 60 psi for approximately 8 h. The catalyst was removed by filtration and the filtrate was concentrated to give 85 g of N-[3S-Amino-2R-hydroxy-4-phenylbutyl]-N'-(1,1-dimethylethyl)-N-(2-methylpropyl)urea as a colorless oil.

EXAMPLE 9

N-[3S-Amino-2R-hydroxy-4-phenylbutyl]-N'-(1,1-dimethylethyl)-N-(3-methylbutyl)urea N-[3S-[N,N-Bis(phenylmethyl)amino]-2R-hydroxy-4-phenylbutyl]-N'-(1,1-dimethylethyl)-N-(3-methylbutyl)urea from Example 7 was hydrogenated following the method of Example 8 to prepare N-[3S-Amino-2R-hydroxy-4-phenylbutyl]-N'-(1,1-dimethylethyl)-N-(3-methylbutyl)urea in comparable yields to Example 8.

EXAMPLE 10

N-benzyl-L-phenylalaninol

METHOD 1:

L-Phenylalaninol (89.51 g, 0.592 moles) was dissolved in 375 mL of methanol under inert atmosphere, 35.52 g (0.592 moles) of glacial acetic acid and 50 mL of methanol was added followed by a solution of 62.83 g (0.592 moles) of benzaldehyde in 100 mL of methanol. The mixture was cooled to approximately 15° C. and a solution of 134.6 g (2.14 moles) of sodium cyanoborohydride in 700 mL of methanol was added in approximately 40 minutes, keeping the temperature between 15° C. and 25° C. The mixture was stirred at room temperature for 18 hours. The mixture was concentrated under reduced pressure and partitioned between 1 L of 2M ammonium hydroxide solution and 2 L of ether. The ether layer was washed with 1 L of 1M ammonium hydroxide solution, twice with 500 mL water, 500 mL of brine and dried over magnesium sulfate for 1 hour. The ether layer was filtered, concentrated under reduced pressure and the crude solid product was recrystallized from 110 mL of ethyl acetate and 1.3 L of hexane to give 115 g (81% yield) of N-benzyl-L-phenylalaninol as a white solid.

METHOD 2:

L-Phenylalaninol (5 g, 33 mmoles) and 3.59 g (33.83 mmoles) of benzaldehyde were dissolved in 55 mL of 3A ethanol under inert atmosphere in a Parr shaker and the mixture was warmed to 60° C. for 2.7 hours. The mixture was cooled to approximately 25° C. and 0.99 g of 5% platinum on carbon was added and the mixture was hydrogenated at 60 psi of hydrogen and 40° C. for 10 hours. The catalyst was filtered off, the product was concentrated under reduced pressure and the crude solid product was recrystallized from 150 mL of heptane to give 3.83 g (48% yield) of N-benzyl-L-phenylalaninol as a white solid.

EXAMPLE 11

N-(t-Butoxycarbonyl)-N-benzyl-L-phenylalaninol

N-benzyl-L-phenylalaninol (2.9 g, 12 mmoles) from Example 10 was dissolved in 3 mL of triethylamine and 27 mL of methanol and 5.25 g (24.1 mmoles) of di-tert-butyl dicarbonate was added. The mixture was warmed to 60° C. for 35 minutes and concentrated under reduced pressure. The residue was dissolved in 150 mL of ethyl acetate and washed twice with 10 mL of cold (0–5° C.), dilute hydrochloric acid (pH 2.5 to 3), 15 mL of water, 10 mL of brine, dried over magnesium sulfate, filtered and concentrated under reduced pressure. The crude product oil was purified by silica gel chromatography (ethyl acetate: hexane, 12:3 as eluting solvent) to give 3.98 g (97% yield) of colorless oil.

EXAMPLE 12

N-(t-Butoxycarbonyl)-N-benzyl-L-phenylalaninal

METHOD 1:

To a solution of 0.32 g (0.94 mmoles) of N-(t-Butoxycarbonyl)-N-benzyl-L-phenylalaninol from Example 11 in 2.8 mL of toluene was added 2.4 mg (0.015 mmoles) of 2,2,6,6-tetramethyl-1-piperidinyloxy, free radical (TEMPO), 0.1 g (0.97 mmoles) of sodium bromide, 2.8 mL of ethyl acetate and 0.34 mL of water. The mixture was cooled to 0° C. and an aqueous solution of 4.2 mL of 5% household bleach containing 0.23 g (3.0 mL, 2.738 mmoles) of sodium bicarbonate was added slowly over 30 minutes. The mixture was stirred at 0° C. for 10 minutes. Three more additions (0.4 mL each) of bleach was added followed by stirring for 10 minutes after each addition to consume all the stating material. The two phase mixture was allowed to separate. The aqueous layer was extracted twice with 8 mL of toluene. The combined organic layer was washed with 1.25 mL of a solution containing 0.075 g of potassium iodide, sodium bisulfate (0.125 g) and water (1.1 mL), 1.25 mL of 10% aqueous sodium thiosulfate solution, 1.25 mL of pH 7 phosphate buffer and 1.5 mL of brine solution. The organic solution was dried over magnesium sulfate, filtered and concentrated under reduced pressure to give 0.32 g (100% yield) of N-(t-Butoxycarbonyl)-N-benzyl-L-phenylalaninal.

METHOD 2:

To a solution of 2.38 g (6.98 mmoles) of N-(t-butoxycarbonyl)-N-benzyl-L-phenylalaninol from Example 11 in 3.8 mL (27.2 mmoles) of triethylamine at 10° C. was added a solution of 4.33 g (27.2 mmoles) of sulfur trioxide pyridine complex in 17 mL of dimethyl sulfoxide. The mixture was warmed to room temperature and stirred for one hour. Water (16 mL) was added and the mixture was extracted with 20 mL of ethyl acetate. The organic layer was washed with 20 mL of 5% citric acid, 20 mL of water, 20 mL of brine, dried over magnesium sulfate and filtered. The filtrate was concentrated under reduced pressure to give 2.37 g (100% yield) of N-(t-Butoxycarbonyl)-N-benzyl-L-phenylalaninal.

EXAMPLE 13

N,αS-Bis(phenylmethyl)-N-(t-butoxycarbonyl)-2S-oxiranemethanamine

METHOD 1:

A solution of 2.5 g (7.37 mmoles) of N-(t-butoxycarbonyl)-N-benzyl-L-phenylalaninal from Example 12 and 0.72 mL of chloroiodomethane in 35 mL of THF was cooled to −78° C. A 4.64 mL of a solution of n-butyllithium (1.6 M in hexane, 7.42 mmoles) was added slowly, keeping the temperature below −70° C. The mixture was stirred for 10 minutes between −70 to −75° C. Two additional portions of 0.22 mL of chloroiodomethane and 1.4 mL of n-butyllithium was added sequentially and the mixture was stirred for 10 minutes between −70 to −75° C. after each addition. Four additional portions of 0.11 mL of chloroiodomethane and 0.7 mL of n-butyllithium was added sequentially and the mixture was stirred for 10 minutes between −70 to −75° C. after each addition. The mixture was warmed to room temperature for 3.5 hours. The product was quenched at below 5° C. with 24 mL of ice-cold water. The biphasic layers were separated and the aqueous layer was extracted twice with 30 mL of ethyl acetate. The combined organic layers was washed three times with 10 mL water, then with 10 mL brine, dried over sodium sulfate, filtered and concentrated under reduced pressure to give 2.8 g of a yellow crude oil. This crude oil (>100% yield) is a mixture of the diastereomeric epoxides N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine. The crude mixture is used directly in the next step without purification.

METHOD 2:

To a suspension of 2.92 g (13.28 mmoles) of trimethylsulfoxonium iodide in 45 mL of acetonitrile was added 1.49 g (13.28 mmoles) of potassium t-butoxide. A solution of 3.0 g (8.85 mmoles) of N-(t-butoxycarbonyl)-N-benzyl-L-phenylalaninal from Example 12 in 18 mL of acetonitrile was added and the mixture was stirred at room temperature for one hour. The mixture was diluted with 150 mL of water and extracted twice with 200 mL of ethyl acetate. The organic layers were combined and washed with 100 mL water, 50 mL brine, dried over sodium sulfate, filtered and concentrated under reduced pressure to give 3.0 g of a yellow crude oil. The crude product was purified by silica gel chromatography (ethyl acetate/hexane: 1:8 as eluting solvent) to give 1.02 g (32.7% yield) of a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine.

METHOD 3:

To a suspension of 0.90 g (4.42 mmoles) of trimethylsulfonium iodide in 18 mL of acetonitrile was added 0.495 g (4.42 mmoles) of potassium t-butoxide. A solution of 1.0 g (2.95 mmoles) of N-(t-butoxycarbonyl)-N-benzyl-L-phenylalaninal from Example 12 in 7 mL of acetonitrile was added and the mixture was stirred at room temperature for one hour. The mixture was diluted with 80 mL of water and extracted twice with 80 mL of ethyl acetate. The organic layers were combined and washed with 100 mL water, 30 mL brine, dried over sodium sulfate, filtered and concentrated under reduced pressure to give 1.04 g of a yellow crude oil. The crude product was a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine.

EXAMPLE 14

3S-[N-(t-Butoxycarbonyl)-N-(phenylmethyl)amino]-1-(2-methylpropyl)amino-4-phenylbutan-2R-ol To a solution of 500 mg (1.42 mmoles) of the crude epoxide from Example 13 in 0.98 mL of isopropanol was added 0.71 mL (7.14 mmoles) of isobutylamine. The mixture was warmed to reflux at 85° C. to 90° C. for 1.5 hours. The mixture was concentrated under reduced pressure and the product oil was purified by silica gel chromatography (chloroform:methanol, 100:6 as eluting solvents) to give 330 mg of 3S-[N-(t-butoxycarbonyl)-N-(phenylmethyl)amino]-1-(2-methylpropyl)amino-4-phenylbutan-2R-ol as a colorless oil (54.5% yield). 3S-[N-(t-Butoxycarbonyl)-N-(phenylmethyl)amino]-1-(2-methylpropyl)amino-4-phenylbutan-2S-ol was also isolated. When purified N,αS-bis(phenylmethyl)-N-(t-butoxycarbonyl)-2S-oxiranemethanamine was used as starting material, 3S-[N-(t-butoxycarbonyl)-N-(phenylmethyl)amino]-1-(2-methylpropyl)amino-4-phenylbutan-2R-ol was isolated after purification by chromatography in an 86% yield.

EXAMPLE 15

N-[3S-[N-(t-Butoxycarbonyl)-N-(phenylmethyl)amino]-2R-hydroxy-4-phenylbutyl]-N'-(1,1-dimethylethyl)-N-(2-methylpropyl)urea To a solution of 309 mg (0.7265 mmoles) of 3S-[N-(t-butoxycarbonyl)-N-(phenylmethyl)amino]-1-(2-methylpropyl)amino-4-phenylbutan-2R-ol from Example 14 in 5 mL of THF was added 0.174 mL (1.5 mmoles) of t-butylisocyanate. The mixture was stirred at room temperature for 1.5 hours. The product was concentrated under reduced pressure to give 350 mg (92% yield) of a white solid crude product. The crude product was purified by silica gel chromatography (ethyl acetate/hexane: 1:4 as eluting solvents) to give 324 mg of N-[3S-[N-(t-butoxycarbonyl)-N-(phenylmethyl)amino]-2R-hydroxy-4-phenylbutyl]-N'-(1,1-dimethylethyl)-N-(2-methylpropyl)urea as a white solid (85.3% yield).

EXAMPLE 16

3S-[N-(t-Butoxycarbonyl)-N-(phenylmethyl)amino]-2S-hydroxy-4-phenylbutyronitrile A solution of 7.0 g (20.65 mmoles) of N-(t-butoxycarbonyl)-N-benzyl-L-phenylalaninal from Example 12 in 125 mL of THF was cooled to −5° C. A solution of 12.96 g of sodium bisulfite in 68 mL of water was added over 40 minutes, keeping the temperature below 5° C. The mixture was stirred for 3 hours at 0 to 5° C. An additional 1.4 g of sodium bisulfite was added and the mixture was stirred for another two hours. Sodium cyanide (3.3 g, 82.56 mmoles) was added to the bisulfite product at 0 to 5° C. and the mixture was stirred at room temperature for 16 hours. The biphasic mixture was extracted with 150 mL of ethyl acetate. The aqueous layer was extracted twice each with 100 mL of ethyl acetate. The combined organic layers was washed twice with 30 mL water, twice with 25 mL brine, dried over sodium sulfate, filtered and concentrated under reduced pressure to give 7.5 g (100% crude yield of both diastereomers) of crude oil. The crude oil was purified by silica gel chromatography (ethyl acetate: hexane, 1:4 as eluting solvents) to give 5.725 g (76% yield) of 3S-[N-(t-butoxycarbonyl)-N-(phenylmethyl)amino]-2S-hydroxy-4-phenylbutyronitrile as the major later eluting diastereomer and 0.73 g (9.6% yield) of 3S-[N-(t-butoxycarbonyl)-N-(phenylmethyl)amino]-2R-hydroxy-4-phenylbutyronitrile as the minor diastereomer. The combined yields of both isomers of cyanohydrins is 85.6% yield.

EXAMPLE 17

3S-[N-(t-Butoxycarbonyl)-N-(phenylmethyl)amino]-1-amino-4-phenylbutan-2R-ol

To a solution of 205.5 mg (0.56 mmoles) of 3S-[N-(t-butoxycarbonyl)-N-(phenylmethyl)amino]-2S-hydroxy-4-phenylbutyronitrile from Example 16 in 4 mL of THF was added 2.4 mL of a solution of borane in THF (1.0 M, 4 mmoles). The mixture was stirred at room temperature for 30 minutes. An additional 1.4 mL of borane in THF was added and the mixture was stirred for another 30 minutes. The mixture was cooled to 0° C. and 2.0 mL of cold (0–5° C.) water was added slowly. The mixture was warmed to room temperature and stirred for 30 minutes. The product was extracted twice with 30 mL of ethyl acetate. The organic layers were combined and washed with 4 mL water, 4 mL brine, dried over sodium sulfate, filtered and concentrated under reduced pressure to give 200 mg of 3S-[N-(t-butoxycarbonyl)-N-(phenylmethyl)amino]-1-amino-4-phenylbutan-2R-ol as a white solid (96.4% yield).

EXAMPLE 18

3S-[N-(t-Butoxycarbonyl)-N-(phenylmethyl)amino]-1-(2-methylpropyl)amino-4-phenylbutan-2R-ol To a solution of 2.41 g (6.522 mmoles) of 3S-[N-(t-butoxycarbonyl)-N-(phenylmethyl)amino]-1-amino-4- phenylbutan-2R-ol from Example 17 in 40 mL of methanol was added 0.592 mL (6.522 mmoles) of isobutyraldehyde and 0.373 mL (6.522 mmoles) of acetic acid. The mixture was stirred for 10 minutes. Sodium cyanoborohydride (1.639 g, 26 mmoles) was added and the mixture was stirred for 16 hours at room temperature. The product mixture was concentrated under reduced pressure and partitioned between 150 mL of ethyl acetate and 50 mL of 1.5M ammonium hydroxide. The organic layer was washed twice with 20 mL water, twice with 20 mL brine, dried over sodium sulfate, filtered and concentrated to an yellow oil. The crude product was purified by silica gel chromatography (chloroform: methanol, 100:6 as eluting solvents) to give 2.326 g of 3S-[N-(t-butoxycarbonyl)-N-(phenylmethyl) amino]-1-(2-methylpropyl)amino-4-phenylbutan-2R-ol as a colorless oil (88.8% yield).

EXAMPLE 19

N-[3S-[N-(t-Butoxycarbonyl)-N-(phenylmethyl) amino]-2R-hydroxy-4-phenylbutyl]-N'-(1,1-dimethylethyl)-N-(2-methylpropyl)urea To a solution of 309 mg (0.7265 mmoles) of 3S-[N-(t-butoxycarbonyl)-N-(phenylmethyl)amino]-1-(2-methylpropyl)amino-4-phenylbutan-2R-ol from Example 18 in 5 mL of THF was added 0.174 mL (1.5 mmoles) of t-butylisocyanate. The mixture was stirred at room temperature for 1.5 hours. The product was concentrated under reduced pressure to give 350 mg (92% yield) of a white solid crude product. The crude product was purified by silica gel chromatography (ethyl acetate/hexane: 1:4 as eluting solvents) to give 324 mg of N-[3S-[N-(t-butoxycarbonyl)-N-(phenylmethyl)amino]-2R-hydroxy-4-phenylbutyl]-N'-(1,1-dimethylethyl)-N-(2-methylpropyl)urea as a white solid (85.3% yield).

EXAMPLE 20

N-[3S-[N-(Phenylmethyl)amino]-2R-hydroxy-4-phenylbutyl]-N'-(1,1-dimethylethyl)-N-(2-methylpropyl)urea To a solution of 210 mg (0.4 mmoles) of N-[3S-[N-(t-Butoxycarbonyl)-N-(phenylmethyl)amino]-2R-hydroxy-4-phenylbutyl]-N'-(1,1-dimethylethyl)-N-(2-methylpropyl) urea from Example 19 in 5.0 mL of THF was added 5 mL of 4N hydrochloric acid. The mixture was stirred at room temperature for two hours. The solvents were removed under reduced pressure to give 200 mg (100%) of N-[3S-[N-(phenylmethyl)amino]-2R-hydroxy-4-phenylbutyl]-N'-(1,1-dimethylethyl)-N-(2-methylpropyl)urea as a white solid.

EXAMPLE 21

N-[3S-Amino-2R-hydroxy-4-phenylbutyl]-N'-(1,1-dimethylethyl)-N-(2-methylpropyl)urea To a solution of 200 mg (0.433 mmoles) of N-[3S-[N-(phenylmethyl)amino]-2R-hydroxy-4-phenylbutyl]-N'-(1,1-dimethylethyl)-N-(2-methylpropyl)urea from Example 20 in 7 mL of 3A ethanol was added 0.05 g of 20% palladium on carbon. The mixture was hydrogenated at 40° C. for 1.8 hours at 5 psi followed by hydrogenation at 60 psi at room temperature for 22 hours. The catalyst was filtered and the solvent and by-product were removed under reduced pressure to give 150 mg (93.4% yield) of N-[3S-amino-2R-hydroxy-4-phenylbutyl]-N'-(1,1-dimethylethyl)-N-(2-methylpropyl)urea as a white solid.

EXAMPLE 22

3S-(N-t-Butoxycarbonyl)amino-4-phenylbutan-1,2R-diol

To a solution of 1 g (3.39 mmoles) of 2S-(N-t-butoxycarbonyl)amino-1S-hydroxy-3-phenylbutanoic acid (commercially available from Nippon Kayaku, Japan) in 50 mL of THF at 0° C. was added 50 mL of borane-THF complex (liquid, 1.0 M in THF), keeping the temperatures below 5° C. The reaction mixture was warmed to room temperature and stirred for 16 hours. The mixture was cooled to 0° C. and 20 mL of water was added slowly to destroy the excess $BH_3$ and to quench the product mixture, keeping the temperature below 12° C. The quenched mixture was stirred for 20 minutes and concentrated under reduced pressure. The product mixture was extracted three times with 60 mL of ethyl acetate. The organic layers were combined and washed with 20 mL of water, 25 mL of saturated sodium chloride solution and concentrated under reduced pressure to give 1.1 g of crude oil. The crude product was purified by silica gel chromatography (chloroform/methanol, 10:6 as eluting solvents) to give 900 mg (94.4% yield) of 3S-(N-t-butoxycarbonyl)amino-4-phenylbutan-1,2R-diol as a white solid.

EXAMPLE 23

3S-(N-t-Butoxycarbonyl)amino-2R-Hydroxy-4-Phenylbut-1-yl Toluenesulfonate

To a solution of 744.8 mg (2.65 mmoles) of 3S-(N-t-butoxycarbonyl)amino-4-phenylbutan-1,2R-diol from Example 22 in 13 mL of pyridine at 0° C. was added 914 mg of toluenesulfonyl chloride in one portion. The mixture was stirred at 0° C. to 5° C. for 5 hours. A mixture of 6.5 mL of ethyl acetate and 15 mL of 5% aqueous sodium bicarbonate solution was added to the reaction mixture and stirred for 5 minutes. The product mixture was extracted three times with 50 mL of ethyl acetate. The organic layers were combined and washed with 15 mL of water, 10 mL of saturated sodium chloride solution and concentrated under reduced pressure to give about 1.1 g of a yellow chunky solid. The crude product was purified by silica gel chromatography (ethyl acetate/hexane 1:3 as eluting solvents) to give 850 mg (74% yield) of 3S-(N-t-butoxycarbonyl)amino-2R-hydroxy-4-phenylbut-1-yl toluenesulfonate as a white solid.

EXAMPLE 24

3S-[N-(t-Butoxycarbonyl)amino]-1-(2-methylpropyl)amino-4-phenylbutan-2R-ol

To a solution of 90 mg (0.207 mmoles) of 3S-(N-t-butoxycarbonyl)amino-2R-hydroxy-4-phenylbut-1-yl toluenesulfonate from Example 23 in 0.143 mL of isopropanol and 0.5 mL of toluene was added 0.103 mL (1.034 mmoles) of isobutylamine. The mixture was warmed to 80 to 85°0 C. and stirred for 1.5 hours. The product mixture was concentrated under reduced pressure at 40 to 50° C. and purified by silica gel chromatography (chloroform/methanol, 10:1 as eluting solvents) to give 54.9 mg (76.8% yield) of 3S-[N-(t-butoxycarbonyl)amino]-1-(2-methylpropyl)amino-4-phenylbutan-2R-ol as a white solid.

EXAMPLE 25

N-[3S-[N-(t-Butoxycarbonyl)amino]-2R-hydroxy-4-phenylbutyl]-N'-(1,1-dimethylethyl)-N-(2-methylpropyl)urea To a solution of 0.1732 g (0.516 mmoles) of 3S-[N-(t-butoxycarbonyl)amino]-1-(2-methylpropyl)amino-4- phenylbutan-2R-ol from Example 24 in 5 mL of ethyl acetate at 0° C. was added 1.62 mL (12.77 mmoles) of t-butylisocyanate and the mixture was stirred for one hour. The product was concentrated under reduced pressure and purified by silica gel chromatography (chloroform/methanol, 100:1.5 as eluting solvents) to give 96 mg (42.9% yield) of N-[3S-[N-(t-butoxycarbonyl)amino]-2R-hydroxy-4-phenylbutyl]-N'-(1,1-dimethylethyl)-N-(2-methylpropyl)urea as a white solid.

EXAMPLE 26

N-[3S-amino-2R-hydroxy-4-phenylbutyl]-N'-(1,1-dimethylethyl)-N-(2-methylpropyl)urea To a solution of 10 mg (0.023 mmoles) of N-[3S-[N-(t-butoxycarbonyl)amino]-2R-hydroxy-4-phenylbutyl]-N'-(1,1-dimethylethyl)-N-(2-methylpropyl)urea from Example 27 in 1 mL of methanol at 0° C. was added 1.05 mL of a 4M hydrogen chloride in methanol and the mixture was stirred at room temperature for 45 minutes. The product was concentrated under reduced pressure. The residue was dissolved 5 mL of methanol and concentrated under reduced pressure. This operation was repeated three times to remove water form the product, after which 8.09 mg (95.2% yield) of N-[3S-amino-2R-hydroxy-4-phenylbutyl]-N'-(1,1-dimethylethyl)-N-(2-methylpropyl)urea hydrochloride salt was obtained as a white solid.

EXAMPLE 27

3S-(N,N-Dibenzyl)amino-2S-hydroxy-4-phenylbutyronitrile, O-trimethylsilyl Ether

To a solution of 24.33 g (73.86 mmol) of 2S-(N,N-dibenzyl)amino-3-phenylpropanal in 740 mL of anhydrous methylene chloride at −20° C. under a nitrogen atmosphere, was added 11.8 mL (8.8 g, 88.6 mmol) of trimethylsilylcyanide, then 19.96 g (88.6 mmol) of anhydrous zinc bromide. After 4 hours at −15° C., and 18 hours at room temperature, the solvent was removed under reduced pressure, ethyl acetate was added, washed with water, brine, dried over magnesium sulfate, filtered and concentrated to afford 31.3 g of a brown oil, which was identified as a 95:5 mixture of 3S-(N,N-dibenzyl)amino-2S-hydroxy-4-phenylbutyronitrile, O-trimethylsilyl ether, m/e=429(M+H) and 3S-(N,N-dibenzyl)amino-2R-hydroxy-4-phenylbutyronitrile, O-trimethylsilyl ether, respectively.

EXAMPLE 28

3S-(N,N-Dibenzyl)amino-2S-hydroxy-4-phenylbutyronitrile

A solution of 10.4 g (24.3 mmol) of the crude 95:5 mixture of 3S-(N,N-dibenzyl)amino-2S-hydroxy-4-phenylbutyronitrile, O-trimethylsilyl ether, and 3S-(N,N-dibenzyl)amino-2R-hydroxy-4-phenylbutyronitrile, O-trimethylsilyl ether from Example 27 in 40 mL of methanol, was added to 220 mL of 1N hydrochloric acid with vigorous stirring. The resulting solid was collected, dissolved in ethyl acetate, washed with aqueous sodium bicarbonate, brine, dried over anhydrous magnesium sulfate, filtered and concentrated to afford 8.04 g of crude product. This was recrystallized from ethyl acetate and hexane to afford pure 3S-(N,N-dibenzyl)amino-2S-hydroxy-4-phenylbutyronitrile, m/e=357 (M+H).

EXAMPLE 29

3S-(N,N-Dibenzyl)amino-2R-hydroxy-4-phenylbutylamine

METHOD 1:

A solution of 20.3 g (47.3 mmol) of the crude 95:5 mixture of 3S-(N,N-dibenzyl)amino-2S-hydroxy-4-phenylbutyronitrile, O-trimethylsilyl ether, and 3S-(N,N-dibenzyl)amino-2R-hydroxy-4-phenylbutyronitrile, O-trimethylsilyl ether from Example 27 in 20 mL of anhydrous diethyl ether, was added to 71 mL (71 mmol) of a 1M solution of lithium aluminum hydride in diethyl ether at reflux. After the addition, the reaction was refluxed for 1 hour, cooled to 0 C, and quenched by the careful addition of 2.7 mL of water, 2.7 mL of 15% aqueous sodium hydroxide, and 8.1 mL of water. The resulting solids were removed by filtration and the filtrate washed with water, brine, dried over magnesium sulfate, filtered and concentrated to afford 13.8 g of crude material, which was recrystallized from tetrahydrofuran and isooctane to afford 10.6 g of 3S-(N,N-dibenzyl)amino-2R-hydroxy-4-phenylbutylamine, mp 46–49 C, m/e=361 (M+H), which was contaminated by approximately 2% of 3S-(N,N-dibenzyl)amino-2S-hydroxy-4-phenylbutylamine.

METHOD 2:

To 15.6 mL (60.4 mmol) of 70% sodium bis(methoxyethoxy)aluminum hydride in toluene, was added 15 mL of anhydrous toluene, and then after cooling to 0 C, a solution of 20.0 g (46 mmol) of the crude 95:5 mixture of 3S-(N,N-dibenzyl)amino-2S-hydroxy-4-phenylbutyronitrile, O-trimethylsilyl ether, and 3S-(N,N-dibenzyl)amino-2R-hydroxy-4-phenylbutyronitrile, O-trimethylsilyl ether from Example 27 in 10 mL of anhydrous toluene, at a rate so as to maintain the temperature below 15° C. After 2.5 hours at room temperature, the reaction was quenched by the careful addition of 200 mL of 5% aqueous sodium hydroxide. The solution was diluted with ethyl acetate, washed with 5% sodium hydroxide, sodium tartrate solution, brine, dried over magnesium sulfate, filtered and concentrated to afford 16.6 g of crude product, which was assayed by HPLC and shown to contain 87% of 3S-(N,N-dibenzyl)amino-2R-hydroxy-4-phenylbutylamine.

EXAMPLE 30

N-[3S-(N,N-Dibenzyl)amino-2R-hydroxy-4-phenylbutyl]-N'-(1,1-dimethylethyl)-N-(3-methylbutyl)urea Step 1:

To a solution of 1.0 g (2.77 mmol) of 3S-(N,N-dibenzyl)amino-2R-hydroxy-4-phenylbutylamine from Example 29 in 4.6 mL of ethanol, was added 0.3 mL (0.24 g, 2.77 mmol) of isovaleraldehyde. After 1 hour at room temperature, the ethanol was removed under reduced pressure, 4 mL of ethyl acetate was added and the solution purged with nitrogen. To the solution was added 360 mg of 5% platinum on carbon catalyst, the solution purged with 40 psig of hydrogen and then maintained under 40 psig of hydrogen for 20 hours. The solution was purged with nitrogen, the catalyst removed by filtration and the solvent removed under reduced pressure to afford 473 mg of the crude product.

Step 2:

The crude product from Step A was directly dissolved in 5.4 mL of ethyl acetate and 109 mg (1.1 mmol) of tertiary-butyl isocyanate was added. After 1 hour at room temperature, the solution was washed with 5% citric acid, brine, dried over magnesium sulfate, filtered and concentrated to afford 470 mg of crude product. The crude product was recrystallized from ethyl acetate and isooctane to afford 160 mg of N-[3S-(N,N-Dibenzyl)amino-2R-hydroxy-4-phenylbutyl]-N'-(1,1-dimethylethyl)-N-(3-methylbutyl)urea, mp 120.4–121.7° C., m/e=530 (M+H).

EXAMPLE 31

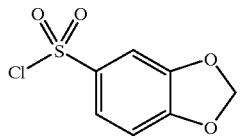

Preparation of 1,3-benzodioxole-5-sulfonyl Chloride

METHOD 1:

To a solution of 4.25 g of anhydrous N,N-dimethylformamide at 0° C. under nitrogen was added 7.84 g of sulfuryl chloride, whereupon a solid formed. After stirring for 15 minutes, 6.45 g of 1,3-benzodioxole was added, and the mixture heated at 100° C. for 2 hours. The reaction was cooled, poured into ice water, extracted with methylene chloride, dried over magnesium sulfate, filtered and concentrated to give 7.32 g of crude material as a black oil. This was chromatographed on silica gel using 20% methylene chloride/hexane to afford 1.9 g of (1,3-benzodioxol-5-yl)sulfonyl chloride.

METHOD 2:

To a 22 liter round bottom flask fitted with a mechanical stirrer, a cooling condenser, a heating mantle and a pressure equalizing dropping funnel was added sulfur trioxide DMF complex (2778 g, 18.1 moles). Dichloroethane (4 liters) was then added and stirring initiated. 1,3-Benzodioxole (1905 g, 15.6 moles) as then added through the dropping funnel over a five minute period. The temperature was then raised to 75° C. and held for 22 hours (NMR indicated that the reaction was done after 9 hours.) The reaction was cooled to 26° and oxalyl chloride (2290 g, 18.1 moles) was added at a rate so as to maintain the temperature below 40° C. (1.5 hours). The mixture was heated to 67° C. for 5 hours followed by cooling to 16° C. with an ice bath. The reaction was quenched with water (5 l) at a rate which kept the temperature below 20° C. After the addition of water was complete, the mixture was stirred for 10 minutes. The layers were separated and the organic layer was washed again twice with water (5 l). The organic layer was dried with magnesium sulfate (500 g) and filtered to remove the drying agent. The solvent was removed under vacuum at 50° C. The resulting warm liquid was allowed to cool at which time a solid began to form. After one hour, the solid was washed with hexane (400 mL), filtered and dried to provide the desired sulfonyl chloride (2823 g). The hexane wash was concentrated and the resulting solid washed with 400 mL hexane to provide additional sulfonyl chloride (464 g). The total yield was 3287 g (95.5% based upon 1,3-benzodioxole).

METHOD 3:

1,4-benzodioxan-6-sulfonyl chloride was prepared according to the procedure disclosed in EP 583960, incorporated herein by reference.

EXAMPLE 32

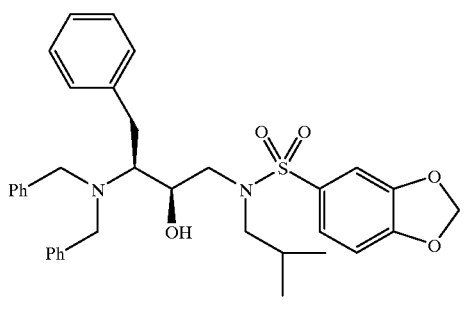

Preparation of 1-[N-[(1,3-benzodioxol-5-yl)sulfonyl]-N-(2-methylpropyl)amino]-3(S)-[bis(phenylmethyl)amine]-4-phenyl-2(R)-butanol

METHOD 1:

To a 5000 mL, 3-necked flask fitted with a mechanical stirrer was added N-[3(S)-[N,N-bis(phenylmethyl)amino]-2(R)-hydroxy-4-phenylbutyl]-N-isobutylamine·oxalic acid salt (WO 96/22275) (354.7 g, 0.7 mole) and 1,4-dioxane (2000 mL). A solution of potassium carbonate (241.9 g, 1.75 moles) in water (250 mL) was then added. The resultant heterogeneous mixture was stirred for 2 hours at room temperature followed by the addition of 1,3-benzodioxole-5-sulfonyl chloride (162.2 g, 0.735 mole) dissolved in 1,4-dioxane (250 mL) over 15 minutes. The reaction mixture was stirred at room temperature for 18 hours. Ethyl acetate (1000 mL) and water (500 mL) were charged to the reactor and stirring continued for another 1 hour. The aqueous layer was separated and further extracted with ethyl acetate (200 mL). The combined ethyl acetate layers were washed with 25% brine solution (500 mL) and dried over anhydrous magnesium sulfate. After filtering and washing the magnesium sulfate with ethyl acetate (200 mL), the solvent in the filtrate was removed under reduced pressure yielding the desired sulfonamide as an viscous yellow foamy oil (440.2 g 105% yield). HPLC/MS (electrospray) (m/z 601 [M+H]+].

EXAMPLE 33

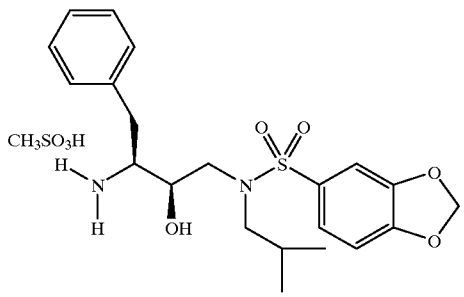

Preparation of 1-[N-[(1,3-benzodioxol-5-yl)sulfonyl]-N-(2-methylpropyl)amino]-3(S)-amino-4-phenyl-2(R)-butanol•methanesulfonic Acid Salt

METHOD 1:

Crude 1-[N-[(1,3-benzodioxol-5-yl)sulfonyl]-N-(2-methylpropyl)amino]-3(S)-[bis(phenylmethyl)amino]-4-phenyl-2(R)-butanol (6.2 g, 0.010 moles) was dissolved in methanol (40 mL). Methanesulfonic acid (0.969 g, 0.010 moles) and water (5 mL) were then added to the solution. The mixture was placed in a 500 mL Parr hydrogenation bottle containing 20% Pd(OH)$_2$ on carbon (255 mg, 50% water content). The bottle was placed in the hydrogenator and purged 5 times with nitrogen and 5 times with hydrogen. The reaction was allowed to proceed at 35° C. with 63 PSI hydrogen pressure for 18 hours. Additional catalyst (125 mg) was added and, after purging, the hydrogenation continued for and additional 20 hours. The mixture was filtered through celite which was washed with methanol (2×10 mL). Approximately one third of the methanol was removed under reduced pressure. The remaining methanol was removed by azeotropic distillation with toluene at 80 torr. Toluene was added in 15, 10, 10 and 10 mL portions. The product crystallized from the mixture and was filtered and washed twice with 10 mL portions of toluene. The solid was dried at room temperature at 1 torr for 6 hours to yield the amine salt (4.5 g, 84%). HPLC/MS (electrospray) was consistent with the desired product (m/z 421 [M+H]$^+$).

METHOD 2:

Part A:

N-[3(S)-[N,N-bis(phenylmethyl)amino]-2(R)-hydroxy-4-phenylbutyl]-N-isobutylamine·oxalic acid salt (2800 g, 5.53 moles) and THF (4 L) were added to a 22 L round bottom flask fitted with a mechanical stirrer. Potassium carbonate (1921 g, 13.9 moles) was dissolved in water (2.8 L) and added to the THF slurry. The mixture was then stirred for one hour. 1,3-benzodioxole-5-sulfonyl chloride (1281 g, 5.8 moles) was dissolved in THF (1.4 L) and added to the reaction mixture over 25 minutes. An additional 200 mL of THF was used to rinse the addition funnel. The reaction was allowed to stir for 14 hours and then water (4 L) was added. This mixture was stirred for 30 minutes and the layers allowed to separate. The layers was removed and the aqueous layer washed twice with THF (500 mL). The combined THF layers were dried with magnesium sulfate (500 g) for one hour. This solution was then filtered to remove the drying agent and used in subsequent reactions.

Part B:

To the THF solution of crude 1-[N-[(1,3-benzodioxol-5-yl)sulfonyl]-N-(2-methylpropyl)amino]-3(S)-[bis(phenylmethyl)amino]-4-phenyl-2(R)-butanol was added water (500 mL) followed by methane sulfonic acid (531g, 5.5 moles). The solution was stirred to insure complete mixing and added to a 5 gallon autoclave. Pearlman's catalyst (200 g of 20% Pd(OH)$_2$ on C/50% water) was added to the autoclave with the aid of THF (500 mL). The reactor was purged four times with nitrogen and four times with hydrogen. The reactor was charged with 60 psig of hydrogen and stirring at 450 rpm started. After 16 hours, HPLC analysis indicated that a small amount of the mono-benzyl intermediate was still present. Additional catalyst (50 g) was added and the reaction was allowed to run overnight. The solution was then filtered through celite (500 g) to remove the catalyst and concentrated under vacuum in five portions. To each portion, toluene (500 mL) was added and removed under vacuum to azeotropically removed residual water. The resulting solid was divided into three portions and each washed with methyl t-butyl ether (2 L) and filtered. The residual solvent was removed at room temperature in a vacuum oven at less than 1 torr to yield the 2714 g of the expected salt.

If desired, the product can be further purified by the following procedure. A total of 500 mL of methanol and 170 g of material from above was heated to reflux until it all dissolved. The solution was cooled, 200 mL of isopropanol added and then 1000–1300 mL of hexane, whereupon a white solid precipitated. After cooling to 0° C., this precipitate was collected and washed with hexane to afford 123 g of the desired material. Through this procedure, the original material which was a 95:5 mixture of alcohol diastereomers was greater than 99:1 of the desired diastereomer.

EXAMPLE 34

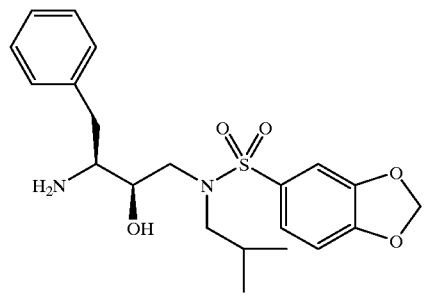

Preparation of 2R-hydroxy-3-[[(1,3-benzodioxol-5-yl)sulfonyl](2-methylpropyl)amino]-1S-(phenylmethyl)propylamine Part A:

Preparation of 2R-hydroxy-3-[[(1,3-benzodioxol-5-yl)sulfonyl](2-methylpropyl)amino]-1S-(phenylmethyl) propylcarbamic acid phenylmethyl ester To a solution of 3.19 g (8.6 mmol) of N-[3S-benzyloxycarbonylamino-2R-hydroxy-4-phenyl]-N-isobutylamine in 40 mL of anhydrous methylene chloride, was added 0.87 g of triethylamine. The solution was cooled to 0° C. and 1.90 g of (1,3-benzodioxol-5-yl)sulfonyl chloride was added, stirred for 15 minutes at 0° C., then for 17 hours at room temperature. Ethyl acetate was added, washed with 5% citric acid, saturated sodium bicarbonate, brine, dried and concentrated to yield crude material. This was recrystallized from diethyl ether/hexane to afford 4.77 g of pure 2R-hydroxy-3-[[(1,3-benzodioxol-5-yl)sulfonyl](2-methylpropyl)amino]-1S-(phenylmethyl)propylcarbamic acid phenylmethyl ester.

Part B:

Preparation of 2R-hydroxy-3-[[(1,3-benzodioxol-5-yl)sulfonyl](2-methylpropyl)amino]-1S-(phenylmethyl) propylamine A solution of 4.11 g of carbamic acid, 2R-hydroxy-3-[[(1,3-benzodioxol-5-yl)sulfonyl](2-methylpropyl)amino]-1S-(phenylmethyl)propyl-, phenylmethyl ester in 45 mL of tetrahydrofuran and 25 mL of methanol was hydrogenated over 1.1 g of 10% palladium-on-carbon under 50 psig of hydrogen for 16 hours. The catalyst was removed by filtration and the filtrate concentrated to afford 1.82 g of the desired 2R-hydroxy-3-[[(1,3-benzodioxol-5-yl)sulfonyl](2-methylpropyl)amino]-1S-(phenylmethyl)propylamine.

From the foregoing detailed description, one skilled in the art can easily ascertain the essential characteristics of this invention, and without departing from the spirit and scope thereof, can make various changes and modifications of the invention to adapt it to various usages and conditions.

As described above, the present invention, referred to above as the continuous in situ synthesis, involves several key features. According to the process, a protected aminoaldehyde, such as may be produced by oxidizing a protected amino alcohol, is flowed into a mixing zone maintained at a temperature below 0° C., at the same time a halomethyl organometallic reagent, either separately added or created in situ from reaction between an organometallic reagent and a dihalomethane (or a mixture of dihalomethanes), also is flowed in the mixing zone in a molar excess relative to said protected aminoaldehyde for contacting in said mixing zone with said protected aminoaldehyde. At the same time, the reaction product(s) of said protected aminoaldehyde and said halomethyl organometallic reagent is(are) withdrawn from said mixing zone, and on warming the reaction product(s), the aminoepoxide forms. Additional specific details of the process can be obtained from Liu, et al., *Organic Process Research & Development*, 1(1): 45–54 (1997), which is hereby incorporated by reference.

By feeding the protected aminoaldehyde to a mixing zone with an appropriate molar amount (excess) of the halomethyl organometallic reagent the length of time needed to complete the reaction with the protected aminoalcohol is significantly diminished while surprisingly limiting the extent of undesired side reactions. The process of the invention allows one to divorce the scale of the mixing zone from the amount of protected aminoaldehyde to be reacted. Thereby, the process permits one to use a small mixing zone, the temperature of which can be easily and carefully controlled, even for the synthesis of multi-kilogram amounts of aminoepoxide.

We claim:

1. In a method of preparing an aminoepoxide wherein a protected aminoaldehyde is reacted with a halomethyl organometallic reagent in an appropriate solvent at a temperature above −80° C., wherein said halomethyl organometallic reagent is formed by reaction between an organometallic reagent and a dihalomethane, the improvement comprising flowing said protected aminoaldehyde into a mixing zone maintained at a temperature below 0° C., also flowing said halomethyl organometallic reagent in said mixing zone for contacting in said mixing zone with said protected aminoaldehyde and also withdrawing from said mixing zone reaction products of said protected aminoaldehyde and said halomethyl organometallic reagent.

2. The method of claim 1 wherein said protected aminoaldehyde is flowed into said mixing zone as a solution with a dihalomethane.

3. The method of claim 2 wherein the organometallic reagent is an organolithium reagent provided in a molar excess relative to said protected aminoaldehyde.

4. The method of claim 3 wherein the organolithium reagent is n-butyl lithium.

5. The method of claim 3 wherein the dihalomethane is selected from bromochloromethane, chloroiodomethane, iodobromomethane, dibromomethane, diiodomethane and bromofluoromethane.

6. The method of claim 5 wherein the mixing zone is maintained at a temperature in a range of −80° C. and 0° C.

7. The method of claim 5 wherein the mixing zone is maintained at a temperature in a range of −40° C. and −15° C.

8. The method of claim 1 wherein separate streams of protected aminoaldehyde, dihalomethane and organometallic reagent are flowed into said mixing zone.

9. The method of claim 8 wherein the organometallic reagent is an organolithium reagent provided in a molar excess relative to said protected aminoaldehyde.

10. The method of claim 9 wherein the dihalomethane is selected from bromochloromethane, chloroiodomethane, iodobromomethane, dibromomethane, diiodomethane and bromofluoromethane.

11. The method of claim 10 wherein the mixing zone is maintained at a temperature in a range of −80° C. and 0° C.

12. The method of claim 10 wherein the mixing zone is maintained at a temperature in a range of −40° C. and −15° C.

13. The method of claim 1 wherein the halomethyl organometallic reagent is a halomethyllithium provided in a molar excess relative to said protected aminoaldehyde.

14. The method of claim 13 wherein the halomethyl organometallic reagent is formed outside of the mixing zone and flowed into the mixing zone for reaction with the protected aminoaldehyde.

15. The method of claim 13 wherein the halomethyl organometallic reagent is formed inside the mixing zone by an in situ reaction between an organolithium reagent and a dihalomethane.

16. The method of claim 14 wherein the dihalomethane is selected from bromochloromethane, chloroiodomethane, iodobromomethane, dibromomethane, diiodomethane and bromofluoromethane.

17. The method of claim 15 wherein the dihalomethane is selected from bromochloromethane, chloroiodomethane, iodobromomethane, dibromomethane, diiodomethane and bromofluoromethane.

* * * * *

UNITED STATES PATENT AND TRADEMARK OFFICE
CERTIFICATE OF CORRECTION

PATENT NO. : 6,127,556
DATED : October 3, 2000
INVENTOR(S) : Chin Liu, *et al.*

It is certified that error appears in the above-identified patent and that said Letters Patent is hereby corrected as shown below:

<u>Title page,</u>
Item [56] References Cited, Other Publications, insert -- International Written Opinion of PCT/US97/22989,(1998). --

Signed and Sealed this

Sixth Day of November, 2001

*Attest:*

*Attesting Officer*

NICHOLAS P. GODICI
*Acting Director of the United States Patent and Trademark Office*